US008383374B2

(12) United States Patent
Causey et al.

(10) Patent No.: US 8,383,374 B2
(45) Date of Patent: Feb. 26, 2013

(54) MATERIALS AND METHODS FOR THE EFFICIENT PRODUCTION OF ACETATE AND OTHER PRODUCTS

(75) Inventors: Thomas B. Causey, Gloucester, MA (US); Lonnie O'Neal Ingram, Gainesville, FL (US); Keelnatham Shanmugam, Gainesville, FL (US); Shengde Zhou, Dekalb, IL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/154,765

(22) Filed: Jun. 7, 2011

(65) Prior Publication Data

US 2011/0281310 A1 Nov. 17, 2011

Related U.S. Application Data

(63) Continuation of application No. 12/235,074, filed on Sep. 22, 2008, now Pat. No. 7,977,075, which is a continuation of application No. 10/703,812, filed on Nov. 6, 2003, now abandoned.

(60) Provisional application No. 60/424,372, filed on Nov. 6, 2002.

(51) Int. Cl.
| | |
|---|---|
| *C12P 7/00* | (2006.01) |
| *C12N 9/00* | (2006.01) |
| *C12N 9/02* | (2006.01) |
| *C12N 9/10* | (2006.01) |
| *C12N 9/14* | (2006.01) |
| *C12N 1/20* | (2006.01) |
| *C12Q 1/68* | (2006.01) |
| *C07H 21/04* | (2006.01) |
| *C07H 21/02* | (2006.01) |
| *C12N 9/04* | (2006.01) |

(52) U.S. Cl. ........ 435/132; 435/183; 435/190; 435/189; 435/6.1; 435/252.3; 435/193; 435/195; 435/252.33; 536/23.2; 536/23.1

(58) Field of Classification Search ........................ None
See application file for complete search history.

(56) References Cited

U.S. PATENT DOCUMENTS

| | | | |
|---|---|---|---|
| 6,013,494 | A | 1/2000 | Nakamura et al. |
| 6,159,738 | A | 12/2000 | Donnelly et al. |
| 7,098,009 | B2 | 8/2006 | Shanmugam et al. |
| 2007/0037265 | A1 | 2/2007 | Zhou et al. |
| 2007/0072280 | A1 | 3/2007 | Cirino et al. |

FOREIGN PATENT DOCUMENTS

| | | |
|---|---|---|
| EP | 0 162 545 | 11/1985 |
| WO | WO 87/03006 | 5/1987 |
| WO | WO 98/10089 | 3/1998 |
| WO | WO 2008/115958 | 9/2008 |
| WO | WO 2008/119009 | 10/2008 |

OTHER PUBLICATIONS

UniProt database. pflB, frdB, frdC, ldhA, atpF, atpH, sucA, poxB and adhE. Retrieved from the internet via www.uniprot.org on Dec. 28, 2011.*
Aristidou, A. A. et al. "Metabolic engineering of *Escherichia coli* to enhance recombinant protein production through acetate reduction," *Biotechnol. Prog.* (1995), vol. 11, pp. 475-478.
Beck, B.J. et al. "Iterative chain elongation by a pikromycin monomodular polyketide synthase" *J. Am. Chem. Soc.* (2003), vol. 125, pp. 4682-4683.
Berraud, C. "Production of highly concentrated vinegar in fed-batch culture," *Biotechnol. lett.* (2000), vol. 22, pp. 451-454.
Causey, T.B. et al. "Engineering *Escherichia coli* W3110 for the conversion of sugar to redox-neutral and oxidized products: Homoacetate production," *Proc. Natl. Acad. Sci.*, USA (2003), vol. 100, pp. 825-832.
Chang, Y. et al. "Expression of *Escherichia coli* pyruvate oxidase (PoxB) depends on the sigma factor encoded by the *rpoS* (*katF*) gene," *Mol. Microbiol.* (1994), vol. 11, pp. 1019-1028.
Chao, Y. and Liao, J.C. "Metabolic responses to substrate futile cycling in *Escherichia coli*," *J. Biol. Chem.* (1994), vol. 269, pp. 5122-5126.
Contiero, J. et al. "Effects of mutations in acetate metabolism on high-cell-density growth of *Escherichia coli*," *J. Ind. Microbiol.* (2000), vol. 24, pp. 421-430.
Datsenko, K.A. et al. "One-step inactivation of chromosomal genes in *Escherichia coli* K-12 using PCR products," *Proc. Natl. Acad. Sci.*, USA (2000), vol. 97, pp. 6640-6645.
Dien, B.S. et al. "Recombinant *Escherichia coli* engineered for the production of L-lactic acid from hexose and pentose sugars" *J. Ind. Microbiol. Biotechnol.* (2001), vol. 27, pp. 259-264.
Farmer, W.R. et al. "Reduction of aerobic acetate production by *Escherichia coil*," *Appl. Environ. Microbiol.* (1997), vol. 63, pp. 3205-3210.
Freer, S.N. "Acetic acid production by *Dekkera/Brettanomyces* yeasts" *World J. Microbiol. Biotechnol.* (2002), vol. 18, pp. 271-275.
Hofmeyer et al. "Regulateing the cellular economy of supply and demand," *FEBS Lett.* (2000), vol. 476, pp. 47-51.
Ingram, L. O. et al. "Enteric Bacterial catalyst for fuel ethanol production" *Biothechnol. Prog.* (1999), vol. 15, pp. 855-866.
Kirkpatrick, C. et al. "Acetate and formate stress: Opposite responses in the proteomes of *Escherichia coli*," *J. Bacteriol.* (2001), vol. 183, pp. 6466-6477.
Koebmann, B.J. et al. "The glycolytic flux in *Escherichia coil* is controlled by the demand for ATP," *J. Bacteriol.* (2002), vol. 184, pp. 3909-3916.
Lasko, D.R. et al. "Bacterial response to acetate challenge: a comparison of tolerance among species," *Appl. Microbiol. Biotechnol.* (2000), vol. 54, pp. 243-247.
Li, Y. et al. "Biotechnological production of pyruvic acid," *Appl. Microbiol. Biotechnol.* (2001), vol. 57, pp. 451-459.

(Continued)

*Primary Examiner* — Yong Pak
(74) *Attorney, Agent, or Firm* — Saliwanchik, Lloyd & Eisenschenk

(57) ABSTRACT

The subject invention provides materials and methods wherein unique and advantageous combinations of gene mutations are used to direct carbon flow from sugars to a single product. The techniques of the subject invention can be used to obtain products from native pathways as well as from recombinant pathways. In preferred embodiments, the subject invention provides new materials and methods for the efficient production of acetate and pyruvic acid.

1 Claim, 9 Drawing Sheets

OTHER PUBLICATIONS

Li, Y. et al. "Efficient pyruvate production by a multi-vitamin auxotroph of *Torulopsis glabrata*: key role and optimization of vitamin levels," *Appl. Microbiol. Biotechnol.* (2001), vol. 55, pp. 680-688.

Ljungdahl, L.G. "The autotrophic pathway of acetate synthesis in acetogenic bacteria," *Ann. Rev. Microbiol.* (1986), vol. 40, pp. 415-450.

Luli, G.W. and R. Strohl "Comparison of growth, acetate production and acetate inhibition of *Escherichia coli* strains in batch and fed-batch fermentations," *Appl. Environ. Microbiol.* (1990), vol. 56, pp. 1004-1011.

Martinez-Morales, F. et al. "Chromosomal integration of heterologous DNA in *Escherichia coli* with precise removal of markers and replicons during construction," *J. Bacteriol.* (1999), vol. 181, pp. 7143-7148.

Niu, W. et al. "Benzene-free synthesis of adipic acid" *Biotechnol. Prog.* (2002), vol. 18, pp. 201-211.

Patnaik, R. et al. "Stimulation of glucose catabolism in *Escherichia coli* by a potential futile cycle," *J. Bacteriol.* (1992), vol. 174, pp. 7527-7532.

Posfai, G. et al. "Versatile insertion plasmids for targeted genome manipulation in bacteria: Isolation, deletion, and rescue of the pathogenicity island LEE of the *Escherichia coli* O157:H7 genome," *J. Bacteriol.* (1997), vol. 179, pp. 4426-4428.

Tomar, A. et al. "The effect of acetate pathway mutations on the production of pyruvate in *Escherichia coli*," *Appl. Microbiol. Biotechnol.* (2003), vol. 62, pp. 76-82.

Tong, I. et al. "1,3-propanediol production by *Escherichia coli* expressing genes from the Klebsiella-pneumoniae-DHA regulon" *Appl. Environ. Microbiol.* (1991), vol. 57, pp. 3541-3546.

Underwood, S. et al. "Genetic changes to optimize carbon partitioning between ethanol and biosynthesis in ethanologenic *Escherichia coli*" *Appl. Environ. Microbiol.* (2002), vol. 68, pp. 6263-6272.

Underwood, S. et al. "Flux through citrate synthase limits the growth of ethanologenic *Escherichia coli* KO11 during xylose fermentation," *Appl. Environ. Microbiol.* (2002), vol. 68, pp. 1071-1081.

Varma, A et al. "Stoichionetric interpretation of *Escherichia coli* glucose catagolism under various oxygenation rates," *Appli. Environ. Microbiol.* (1993), vol. 59, pp. 2465-2473.

Wang et al. "Directed evolution of metabolically engineered *Escherichia coil* for carotenoid production" *Biotechnol. Prog.* (2000), vol. 16, pp. 922-926.

Yokota, A. et al. Pyruvic acid production by an $F_1$-ATPase-defective mutant of *Escherichia coli* W1485*lip2*: *Biosci. Biotech. Biochem.* (1994), vol. 58, pp. 2164-2167.

Zhou, S. et al. "Production of optically pure D-lactic acid in mineral salts medium by metabolically engineered *Escherichia coli* W3110" *Appl. Environ. Microbiol.* (2003), vol. 69, pp. 399-407.

Cover page of J. Bacteriol. 2001, November, pp. 6466-6477, vol. 183, No. 21.

Causey, T. B. et al. "Engineering *Escherichia coil* for efficient conversion of glucose to pyruvate," *PNAS*, Feb. 24, 2004, vol. 101, No. 8, pp. 2235-2240, XP-002519088.

Girbal, L. et al. "Regulation of *Clostridium acetobutylicum* Metabolism as Revealed by Mixed-Substrate Steady-State Continuous Cultures: Role of NADH/NAD Ratio and ATP Pool" *Journal of Bacteriology*, Nov. 1994, vol. 176, No. 21, pp. 6433-6438, XP-002519087.

Stewart, J. D. et al. "A Chemist's Perspective on the Use of Genetically Engineered Microbes as Reagents for Organic Synthesis" *Biotechnology and Genetic Engineering Reviews*, Apr. 1997, pp. 67-143, vol. 14.

Klegg Database, Pyruvate Metabolism, TCA cycle and *E. coli* acetate kinase A, fumarate reductase, pyruvate formate lyase, 2-ketoglutarate dehydrogenase, D-lactate dehydrogenase, pyruvate dehydrogenase, ATP synthease and alcohol/aldehyde dehydrogenase. Retrieved from http://www.geonome.jp/dbget-bin on 4/26/20006.

\* cited by examiner

MATERIALS AND METHODS FOR THE EFFICIENT PRODUCTION OF ACETATE AND OTHER PRODUCTS

CROSS-REFERENCE TO RELATED APPLICATIONS

This application is a continuation of U.S. application Ser. No. 12/235,074, filed Sep. 22, 2008, which is a continuation of U.S. application Ser. No. 10/703,812, filed Nov. 6, 2003, which claims the benefit of U.S. Provisional Application Ser. No. 60/424,372, filed Nov. 6, 2002.

The subject invention was made with government support under research projects supported by USDA/NRI, Grant No. 2001-35504-10669; USDA/IFAS, Grant No. 00-52104-9704; and USDOE Grant No. FG02-96ER20222. The government has certain rights in this invention.

BACKGROUND OF INVENTION

Recent trends toward the production of "green" chemicals will require development of innovative synthesis techniques that are highly efficient and cost effective.

Throughout the past decade, a number of traditional chemical companies in the United States and Europe have begun to develop infrastructures for the production of compounds using biocatalytic processes. Considerable progress has been reported toward new processes for commodity chemicals such as ethanol (Ingram, L. O., H. C. Aldrich, A. C. C. Borges, T. B. Causey, A. Martinez, F. Morales, A. Saleh, S. A. Underwood, L. P. Yomano, S. W. York, J. Zaldivar, and S. Zhou, 1999 "Enteric bacterial catalyst for fuel ethanol production" *Biotechnol. Prog.* 15:855-866; Underwood, S. A., S. Zhou, T. B. Causey, L. P. Yomano, K. T. Shanmugam, and L. O. Ingram, 2002 "Genetic changes to optimize carbon partitioning between ethanol and biosynthesis in ethanologenic *Escherichia coli." Appl. Environ. Microbiol.* 68:6263-6272), lactic acid (Zhou, S., T. B. Causey, A. Hasona, K. T. Shanmugam and L. O. Ingram, 2003 "Production of optically pure D-lactic acid in mineral salts medium by metabolically engineered *Escherichia coli* W3110*" Appl. Environ. Microbiol.* 69:399-407; Chang, D., S. Shin, J. Rhee, and J. Pan, 1999 "Homofermentative production of D- or L-lactate in metabolically engineered *Escherichia coli* RR1*" Appl. Environ. Microbiol.* 65:1384-1389; Dien, B. S., N. N. Nichols, and R. J. Bothast, 2001 "Recombinant *Escherichia coli* engineered for the production of L-lactic acid from hexose and pentose sugars" *J. Ind Microbiol. Biotechnol.* 27:259-264), 1,3-propanediol (Nakamura, U.S. Pat. No. 6,013,494; Tong, I., H. H. Liao, and D. C. Cameron, 1991 "1,3-propanediol production by *Escherichia coli* expressing genes from the *Klebsiella-pneumoniae*-DHA regulon" *App. Env. Microbiol.* 57:3541-3546), and adipic acid (Niu, W., K. M. Draths, and J. W. Frost, 2002 "Benzene-free synthesis of adipic acid" *Biotechnol. Prog.* 18:201-211).

In addition, advances have been made in the genetic engineering of microbes for higher value specialty compounds such as acetate, polyketides (Beck, B. J., C. C. Aldrich, R. A. Fecik, K. A. Reynolds, and D. H. Sherman, 2003 "Iterative chain elongation by a pikromycin monomodular polyketide synthase" *J. Am. Chem. Soc.* 125:4682-4683; Dayem, L. C., J. R. Carney, D. V. Santi, B. A. Pfeifer, C. Khosla, and J. T. Kealey, 2002 "Metabolic engineering of a methylmalonyl-CoA mutase—epimerase pathway for complex polyketide biosynthesis in *Escherichia coli." Biochem.* 41:5193-5201) and carotenoids (Wang, Chia-wei, Min-Kyu Oh, J. C. Liao, 2000 "Directed evolution of metabolically engineered *Escherichia coli* for carotenoid production" *Biotechnol. Prog.* 16:922-926).

Acetic acid, a widely used specialty chemical in the food industry, has recently emerged as a potential bulk chemical for the production of plastics and solvents. Acetic acid has been produced using microbial systems; however, the production of acetic acid in microbial systems competes with the production of $CO_2$ and cell mass. Thus, while efficient acetate-producing microbial systems are important for industrial uses, the systems must have an increased output of acetate with a decreased input of expensive microbial nutrients.

The biological production of acetic acid has been largely displaced by petrochemical routes as the uses for this commodity chemical have expanded from food products to plastics, solvents, and road de-icers (Freer, S. N., 2002 "Acetic acid production by *Dekkera/Brettanomyces* yeasts" *World J. Microbiol. Biotechnol.* 18:271-275). In 2001, the world production of acetic acid reached an estimated 6.8 million metric tons, half of which was produced in the United States.

Previously, three microbial approaches have been explored for acetic acid production. In the two-step commercial process, sugars are fermented to ethanol by *Saccharomyces* yeast. Then, the resulting beers are oxidized to acetic acid by *Acetobacter* under aerobic conditions (Berraud, C., 2000 "Production of highly concentrated vinegar in fed-batch culture" *Biotechnol. Lett.* 22:451-454; Cheryan, M., S. Parekh, M. Shah, and K. Witjitra, 1997 "Production of acetic acid by *Clostridium thermoaceticum" Adv. Appl. Microbial.* 43:1-33). Using this process, acetic acid titres of around 650 mM are typically produced; however, higher titres can be readily achieved by the addition of complex nutrients in fed-batch processes requiring 60-120 hours. Overall yields for this commercial process have been estimated to be 76% of the theoretical maximum (2 acetate per glucose; 0.67 g acetic acid per g glucose).

Under a second approach, carbohydrates can be anaerobically metabolized to acetic acid at substantially higher yields (3 acetates per glucose) by Clostridia that contain the Ljungdahl-Wood pathway for acetogenesis (Berraud, C., 2000 "Production of highly concentrated vinegar in fed-batch culture" *Biotechnol. Lett.* 22:451-454; Ljungdahl, L. G., 1986 "The autotrophic pathway of acetate synthesis in acetogenic bacteria" *Ann. Rev. Microbiol.* 40:415-450). In particular, *Clostridium thermoaceticum* containing the Ljungdahl-Wood pathway produces high yields of acetic acid (Cheryan, M., S. Parekh, M. Shah, and K. Witjitra, 1997 "Production of acetic acid by *Clostridium thermoaceticum" Adv. Appl. Microbial.* 43:1-33).

Recently, Freer (Freer, S. N., 2002 "Acetic acid production by *Dekkera/Brettanomyces* yeasts" *World J. Microbial. Biotechnol.* 18:271-275) identified yeast strains (*Dekkera* and *Brettanomyces*) that produce acetic acid as a primary product from glucose for potential use in acetic acid production. All three of these current microbial acetic acid production systems require complex nutrients, which increase the cost of materials, acetate purification, and waste disposal.

*Escherichia coli* is widely used as a biocatalyst for high value products such as recombinant proteins (Akesson, M., P. Hagander, and J. P. Axelsson, 2001 "Avoiding acetate accumulation in *Escherichia coli* cultures using feedback control of glucose feeding" *Biotechnol. Bioeng.* 73:223-230; Aristidou, A. A., K. San, and G. N. Bennett, 1995 "Metabolic engineering of *Escherichia coli* to enhance recombinant protein production through acetate reduction" *Biotechnol. Prog.* 11:475-478; Contiero, J., C. Beatty, S. Kumar, C. L. DeSanti, W. R. Strohl, and A. Wolfe, 2000 "Effects of mutations in acetate metabolism on high-cell-density growth of *Escherichia coli*" *J. Ind. Microbiol.* 24:421-430; Luli, G. W. and R. Strohl, 1990 "Comparison of growth, acetate production and acetate inhibition of *Escherichia coli* strains in batch and fed-batch fermentations" *Appl. Environ. Microbiol.* 56:1004-1011) and amino acids (Chotani, G., T. Dodge, A. Hsu, M. Kumar, R. LaDuca, D. Trimbur, W. Weyler, and K. Sanford, 2000 "The commercial production of chemicals using pathway engineering" *Biochem. Biophys. Acta* 1543:434-455; Eggeling, L., W. Pfefferle, and H. Sahm, 2001 "Amino acids," p. 281-304 in C. Ratledge and B. Kristiansen (ed.), Basic Biotechnology, 2" edition. Cambridge University Press. Cambridge, U.K.).

*Escherichia coli* generate acetyl-CoA during fermentative and oxidative metabolism, which the cell then uses to produce small amounts of acetate (Akesson, M., P. Hagander, and J. P. Axelsson, 2001 "Avoiding acetate accumulation in *Escherichia coli* cultures using feedback control of glucose feeding" *Biotechnol. Bioeng.* 73:223-230; Contiero, J., C. Beatty, S. Kumar, C. L. DeSanti, W. R. Strohl, and A. Wolfe, 2000 "Effects of mutations in acetate metabolism on high-cell-density growth of *Escherichia coli*" *J. Ind. Microbiol.* 24:421-430).

Many *E. coli* strains grow well in simple mineral salts medium and readily metabolize all of the hexose and pentose sugar constituents of plant biomass (Ingram, L. O., H. C. Aldrich, A. C. C. Borges, T. B. Causey, A. Martinez, F. Morales, A. Saleh, S. A. Underwood, L. P. Yomano, S. W. York, J. Zaldivar, and S. Zhou, 1999 "Enteric bacterial catalyst for fuel ethanol production" *Biotechnol. Prog.* 15:855-866). During aerobic and anaerobic carbohydrate metabolism, acetate is typically produced as a minor product. Recent successes have been reported in the engineering of *E. coli* strains for commodity chemicals such as propanediol (Nakamura, C. E., A. A. Gatenby, Hsu, A. K.-H., R. D. LaReau, S. L. Haynie, M. Diaz-Torres, D. E. Trimbur, G. M. Whited, V. Nagarajan, M. S. Payne, S. K. Picataggio, and R. V. Nair, 2000 "Method for the production of 1,3-propanediol by recombinant microorganisms" U.S. Pat. No. 6,013,494; Tong, I., H. H. Liao, and D. C. Cameron, 1991 "1,3-propanediol production by *Escherichia coli* expressing genes from the *Klebsiella-pneumoniae*-DHA regulon" *App. Env. Microbiol.* 57:3541-3546), adipic acid (Niu, W., K. M. Draths, and J. W. Frost, 2002 "Benzene-free synthesis of adipic acid" *Biotechnol. Prog.* 18:201-211), lactic acid (Chang, D., S. Shin, J. Rhee, and J. Pan, 1999 "Homofermentative production of D- or L-lactate in metabolically engineered *Escherichia coli* RR1" *Appl. Environ. Microbiol.* 65:1384-1389; Dien, B. S., N. N. Nichols, and R. J. Bothast, 2001 "Recombinant *Escherichia coli* engineered for the production of L-lactic acid from hexose and pentose sugars" *J. Ind Microbiol. Biotechnol.* 27:259-264), succinic acid (Donnelly, M. I., C. Sanville-Millard, and R. Chatterjee, 1998 "Method for construction of bacterial strains with increased succinic acid production" U.S. Pat. No. 6,159,738; Vemuri, G. N., M. A. Altman, and E. Altman, 2002 "Effects of growth mode and pyruvate carboxylase on succinic acid production by metabolically engineered strains of *Escherichia coli*" *J. Bacteria* 68:1715-1727), and ethanol (Ingram, L. O., H. C. Aldrich, A. C. C. Borges, T. B. Causey, A. Martinez, F. Morales, A. Saleh, S. A. Underwood, L. P. Yomano, S. W. York, J. Zaldivar, and S. Zhou, 1999 "Enteric bacterial catalyst for fuel ethanol production" *Biotechnol. Prog.* 15:855-866). In using these aerobic and anaerobic processes, the resultant production of acetate by the native pathway (phosphotransacetylase and acetate kinase) has generally been regarded as an undesirable consequence of excessive glycolytic flux (Akesson, M., P. Hagander, and J. P. Axelsson, 2001 "Avoiding acetate accumulation in *Escherichia coli* cultures using feedback control of glucose feeding" *Biotechnol. Bioeng.* 73:223-230; Aristidou, A. A., K. San, and G. N. Bennett, 1995 "Metabolic engineering of *Escherichia coli* to enhance recombinant protein production through acetate reduction" *Biotechnol. Prog.* 11:475-478; Contiero, J., C. Beatty, S. Kumar, C. L. DeSanti, W. R. Strohl, and A. Wolfe, 2000 "Effects of mutations in acetate metabolism on high-cell-density growth of *Escherichia coli*" *J. Ind, Microbiol.* 24:421-430; Farmer, W. R., and J. C. Liao, 1997 "Reduction of aerobic acetate production by *Escherichia coli* 1997" *Appl. Environ. Microbiol.* 63:3205-3210).

Chao and Liao (Chao, Y., and J. C. Liao, 1994 "Metabolic responses to substrate futile cycling in *Escherichia coli*" *J. Biol. Chem.* 269:5122-5126) and Patnaik et al. (Patnaik, R., W. D. Roof, R. F. Young, and J. C. Liao, 1992 "Stimulation of glucose catabolism in *Escherichia coli* by a potential futile cycle" *J. Bacteriol.* 174:7525-7532) demonstrated a 2-fold stimulation of glycolytic flux in *E. coli* using plasmids to express genes that created futile cycles to consume ATP.

Recently, Koebmann et al. (Koebmann, B. J., H. V. Westerhoff, J. L. Snoep, D. Nilsson, and P. R. Jensen, 2002 "The glycolytic flux in *Escherichia coli* is controlled by the demand for ATP" *J. Bacteriol.* 184:3909-3916) independently concluded that glycolytic flux is limited by ATP utilization during the oxidative metabolism of glucose. In their studies, flux increased in a dose-dependent manner with controlled expression of $F_1$ ATPase from a plasmid. Thus glycolytic flux appears to be regulated by the economy of supply and demand as proposed by Hofmeyer and Cornish-Bowden (Hofmeyer, J.-H. S., and A. Cornish-Bowden, 2000 "Regulating the cellular economy of supply and demand" *FEBS Lett.* 467:47-51).

Currently, only the two-part commercial process, the Ljungdahl-Wood pathway-containing Clostridia, as well as special yeast strains have been investigated as potential biocatalysts for the production of acetate. Due to the competing production of dicarboxylic acids and cell mass from glucose, the level of acetate production using these methods has been relatively low. Indeed, none of these methods have been reported to grow and produce acetate efficiently in mineral salts media containing sugar. In fact, each of these methods requires the use of complex nutrients, which ultimately increases the cost of materials, acetate purification, and waste disposal. Therefore, a need remains for better biocatalysts that efficiently produce acetate and other fermentation products using a mineral salts medium.

Pyruvic acid is currently manufactured for use as a food additive, nutriceutical, and weight control supplement (Li, Y., J. Chen, and S.-Y. Lun, 2001 "Biotechnological production of pyruvic acid" *Appl. Microbiol, Biotechnol.* 57:451-459). Pyruvic acid can also be used as a starting material for the synthesis of amino acids such as alanine, tyrosine, phenylalanine, and tryptophan and for acetaldehyde production.

Pyruvate is produced commercially by both chemical and microbial processes. Chemical synthesis involves the decarboxylation and dehydration of calcium tartrate, a by-product of the wine industry. This process involves toxic solvents and is energy intensive with an estimated production cost of $8,650 per ton of pyruvate. Microbial pyruvate production is based primarily on two microorganisms, a multi-vitamin auxotroph of the yeast *Torulopsis glabrata* (Li, Y., J. Chen, and S.-Y. Lun, and X. S. Rui, 2001 "Efficient pyruvate production by a multi-vitamin auxotroph of *Torulopsis glabrata*: key role and optimization of vitamin levels" *Appl. Microbiol. Biotech-* nol. 55:680-68) and a lipoic acid auxotroph of *Escherichia coli* containing a mutation in the $F_1$ ATPase component of $(F_1F_0)H^+$-ATP synthase (Yokota, A., Y. Terasawa, N. Takaoka, H. Shimizu, and F. Tomita, 1994 "Pyruvic acid production by an $F_1$-ATPase-defective mutant of *Escherichia coli* W1485lip2" *Biosci. Biotech, Biochem.* 58:2164-2167). Both of these production strains require precise regulation of media composition during fermentation and complex supplements. The estimated production costs of pyruvate production by microbial fermentation with these strains is estimated to be 14.5% ($1,255 per ton pyruvate) of that for chemical synthesis.

Recently, Tomar et al. (Tomar, A., M. A. Eiteman, and E. Altman, 2003 "The effect of acetate pathway mutations on the production of pyruvate in *Escherichia coli*." *Appl. Microbiol. Biotechnol.* 62:76-82.2003) have described a new mutant strain of *E. coli* for pyruvate production. This strain contains three mutations, ppc (phosphoenolpyruvate carboxylase), aceF (pyruvate dehydrogenase), and adhE (alcohol dehydrogenase) and is capable of producing 0.65 grams pyruvate per gram of glucose using complex media supplemented with acetate.

Typical production rates of pyruvate for biocatalysts are around $1 \text{ g L}^{-1} \text{ h}^{-1}$ with yields exceeding half the weight of substrate. *Torulopsis glabrata*, the yeast strain currently used for the commercial production of pyruvate, can achieve pyruvate titers of $69 \text{ g L}^{-1}$. As noted above, *T. glabrata* strains used in the commercial process are multivitamin auxotrophs requiring tight regulation of vitamin concentrations which result in complex vitamin feeding strategies during fermentation (Li, Y., J. Chen, and S.-Y. Lun, 2001 "Biotechnological production of pyruvic acid" *Appl. Microbiol. Biotechnol.* 57:451-459). Previous *E. coli* strains constructed for pyruvate production were cultured in complex media and have been plagued by low titers and yields (Tomar, A. et al. 2003, "The effect of acetate pathway mutations on the production of pyruvate in *Escherichia coli*." *Appl. Microbiol. Biotechnol.* 62:76-82; Yokota A. et al., 1994 "Pyruvic acid production by an $F_1$-ATPase-defective mutant of *Escherichia coli* W1485lip2." *Biosci. Biotech. Biochem.* 58:2164-6167).

Nutrients in culture medium often represent a major cost associated with commercial fermentations. The use of a mineral salts medium and inexpensive carbon source offers the potential to improve the economics of many biological processes by reducing the costs of materials, product purification, and waste disposal (Zhang, J. and R. Greasham, 1999. *Appl. Microbiol. Biotechnol.* 51:407-421).

There is a need in the art to identify and develop new, efficient, and environmentally friendly processes for producing specialty compounds.

BRIEF SUMMARY

The subject invention provides materials and methods wherein unique and advantageous combinations of gene mutations are used to direct carbon flow from sugars to a desired product. The techniques of the subject invention can be used to obtain products from native pathways as well as from recombinant pathways.

The materials and methods of the subject invention can be used to produce a variety of products with only mineral salts and sugar as nutrients. Useful products include pure acetic acid; 1,3-propanediol; 2,3-propanediol; pyruvate; dicarboxylic acids; adipic acid; amino acids, including aliphatic and aromatic amino acids; and alcohols including ethanol, butanol, isopropanol, and propanol. In preferred embodiments, the subject invention provides new materials and methods for the efficient production of acetate. In further preferred embodiments, the subject invention provides advantageous biocatalysts for acetate production and for pyruvate production.

In a specific embodiment, the subject invention provides a recombinant derivative of *Escherichia coli* W3110 that contains six chromosomal deletions (focA-pflB frdBC ldhA atpFH sucA adhE). The resulting strain (TC36) exhibits approximately a 2-fold increase in maximal rates of acetate production (specific and volumetric) over W3110. This increase can be attributed to the mutation in the $(F_1F_0)H^+$-ATP synthase, which eliminates ATP production by oxidative phosphorylation while retaining cytoplasmic $F_1$-ATP synthase for the gratuitous consumption of ATP.

TC36 produces acetic acid in mineral salts medium containing glucose with a yield of 68% of the maximum theoretical yield using native pathways (two acetates per glucose). Advantageously, TC36 is devoid of plasmids and antibiotic resistance genes.

Further embodiments of the subject invention provide additional derivatives of *Escherichia coli* W3110 as new biocatalysts for the production of homo-acetate. In one embodiment, homo-acetate production by the new strain, TC36, approaches the theoretical maximum of two acetates per glucose. Eliminating the fermentation pathways of W3110 resulted in the new strain SZ47 and doubled the loss of carbon as volatile products. While the rate of acetate production decreased in SZ47 as compared to W3110, the cell yield increased. The inactivation of oxidative phosphorylation (ΔatpFH) in SZ47 to produce TC24 resulted in a 5-fold increase in acetate yield and a 3-fold improvement in carbon recovery.

In accordance with the subject invention, competing pathways are eliminated by chromosomal inactivation of genes encoding lactate dehydrogenase, pyruvate formatelyase, and fumarate reductase (Δ(focA-pflB)::FRT ΔfrdBC ΔldhA), $(F_1F_0)H^+$-ATP synthase (atpFH), alcohol/aldehyde dehydrogenase (adhE), and 2-ketoglutarate dehydrogenase (sucA), which increases the production of acetate.

Using a simple two-step batch feeding strategy can increase acetate production. Specifically, a second addition of 3% glucose added at the end of the growth phase (12 h) and metabolized to completion results in 78% of the theoretical maximum. A further increase in acetate production can be obtained by combining the two-step batch feeding strategy with a nitrogen limitation, which results in 86% of the theoretical maximum.

The subject invention provides a method to reduce the loss of substrate carbon into cell mass and/or into carbon dioxide. Also, the subject invention provides a method to reduce oxygen demand during bioconversion process.

The use of mineral salts medium, lack of antibiotic resistance genes or plasmids, high yield of homo-acetate, and high product purity achieved according to the subject invention are advantageous because of reduced costs associated with nutrients, purification, containment, BOD, and waste treatment.

In an alternative embodiment, the subject invention provides a new biocatalyst for the efficient production of pyruvate from glucose that requires only simple mineral salts as nutrients.

BRIEF DESCRIPTION OF THE SEQUENCES

Figures 1A, 1B, 1C:
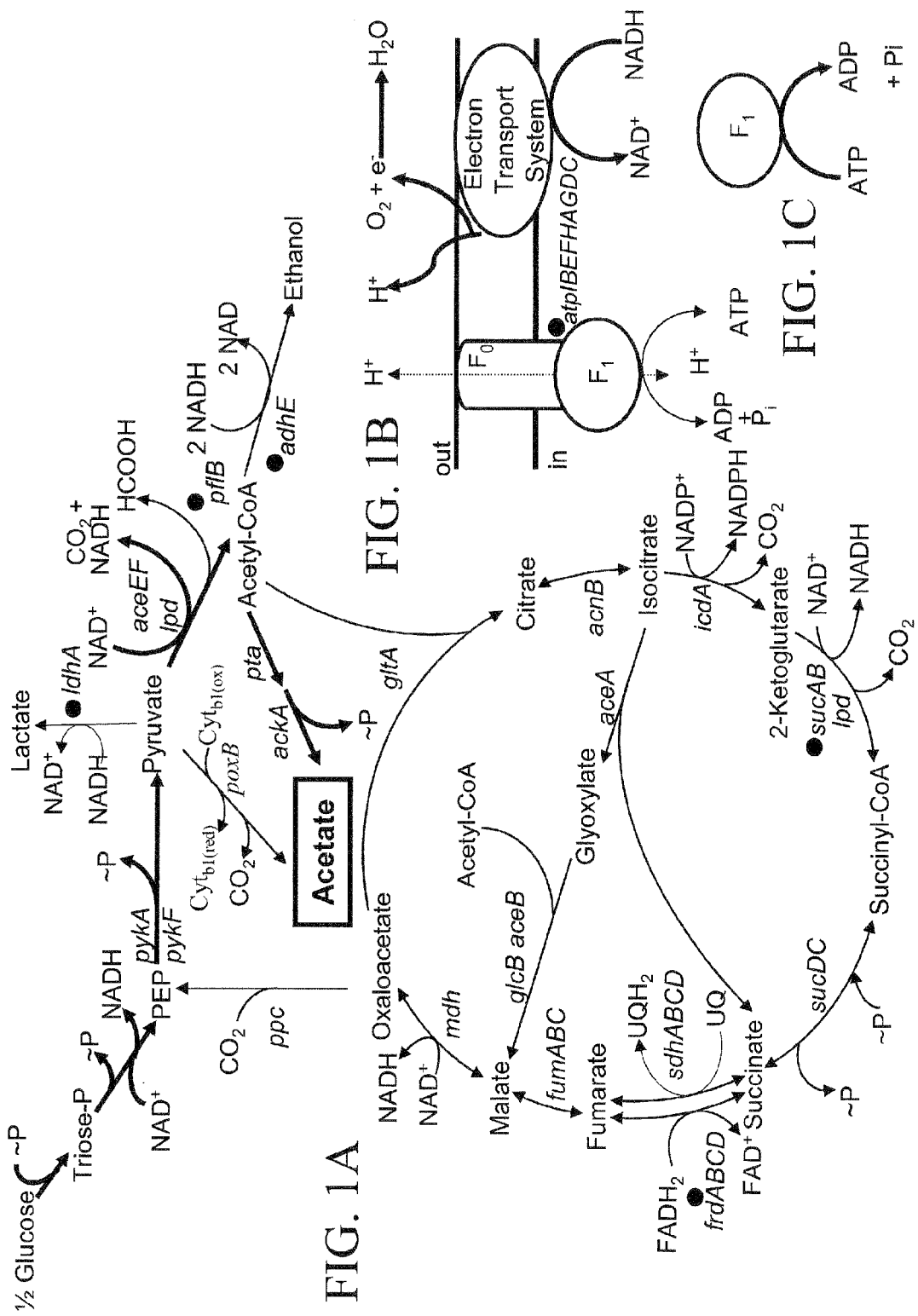
FIGS. 1A-1C Diagram summarizing genetic modifications used to redirect glucose metabolism to acetate. Bold arrows mark principle metabolic routes in TC36. Reactions which have been blocked by gene deletions in TC36 are marked with solid circles. Genes encoding enzymes are shown in italics. A. Central carbon metabolism. Bold arrows indicate the primary pathway for acetate production from glucose in TC36. This strain produces a net of 4 ATP equivalents (~P) per glucose molecule. B. Oxidative phosphorylation. The ATPsynthase is inactive in TC36 although the electron transport system remains functional as the primary route for NADH oxidation in TC36 (bold arrows). C. $F_1$-ATPase remains active in TC36 for the regeneration of ADP but lacks subunits for membrane assembly.

SEQ ID NO:1 is a sense primer used according to the subject invention.

SEQ ID NO:2 is an antisense primer used according to the subject invention.

DETAILED DISCLOSURE

The subject invention provides materials and methods wherein unique and advantageous combinations of gene mutations are used to direct carbon flow to a desired product. The techniques of the subject invention can be used to obtain products from native pathways as well as from recombinant pathways.

Advantageously, the subject invention provides a versatile platform for the production of a variety of products with only mineral salts and sugar as nutrients. Useful products include pure acetic acid; 1,3-propanediol; 2,3-propanediol; pyruvate; dicarboxylic acids; adipic acid; and amino acids, including aliphatic and aromatic amino acids. In preferred embodiments, the subject invention provides new materials and methods for the efficient production of acetate.

In preferred embodiments, the subject invention provides strains of *E. coli* (lacking plasmids and antibiotic resistance genes) as biocatalysts for the production of chemically pure acetate and/or pyruvate. Unlike other acetate-producing microbial systems, the subject invention can employ a single step process using sugars as substrates, high rates of acetate production (almost two-fold higher), high acetate yields, simple nutrition requirements (mineral salts medium), and a robust metabolism permitting the bioconversion of hexoses, pentoses, and many dissacharides.

Specifically exemplified herein is a new *E. coli* biocatalyst containing six chromosomal deletions (ΔfocApflB ΔfrdCD ΔldhA ΔatpFH ΔsucA ΔadhE). The resulting strain (TC36) contains no plasmids or antibiotic resistance genes and produces high yields of acetate from glucose in a mineral salts medium.

Further embodiments of the subject invention provide additional derivatives of *Escherichia coli* W3110 as new biocatalysts for the production of acetate. Eliminating the fermentation pathways of W3110 resulted in the new strain SZ47 and doubled the loss of carbon as volatile products. While the rate of acetate production decreased in SZ47 as compared to W3110, the cell yield increased. The inactivation of oxidative phosphorylation (ΔatpFH) in SZ47 to produce TC24 resulted in a 5-fold increase in acetate yield and a 3-fold improvement in carbon recovery. Homo-acetate production by the new strain, TC36, approaches the theoretical maximum of two acetates per glucose.

The methods of the subject invention are particularly advantageous because, in a preferred embodiment, deletions (rather than mutations which simply change a sequence) are used to inactivate pathways. Deletions provide maximum stability; with deletions, there is no opportunity for a reverse mutation to restore function. Please note, however, that as used herein, "mutations" includes changes in sequence or deletions unless the context clearly indicates otherwise. Such changes or deletions in polynucleotide sequences are also referred to herein as genetic "modifications."

For optimal acetate production in accordance with a specific embodiment of the subject invention, deletions in W3110 that inactivate oxidative phosphorylation (ΔatpFH), disrupt the cyclic function of the tricarboxylic acid cycle (ΔsucA), and eliminate all major fermentation pathways (ΔfocA-pflB, ΔfrdBC, ΔldhA, ΔadhE) are combined. One such strain, TC36, metabolizes sugars to acetate with the efficiency of fermentative metabolism, diverting a minimum of carbon to cell mass (biocatalyst) and $CO_2$, which results in extremely high product yields.

For improved acetic acid yields, a simple two-step batch feeding strategy can be used in which a second addition of 3% glucose is added at the end of the growth phase (12 h). Further improved acetic acid yields can be obtained by combining this two-step batch feeding strategy with a nitrogen limitation.

Although production of homo-acetate using a recombinant gene is specifically exemplified herein, those skilled in the art having the benefit of the subject disclosure could utilize other genes (single genes or combinations), to produce alternative oxidized or reduced products.

The choice of genes for inactivation of competing fermentation pathways, as described herein, is important to maximize yield and minimize nutritional requirements. For example, carbohydrates can be anaerobically metabolized to acetic acid at substantially higher yields (3 acetates per glucose) by Clostridia (anaerobic) that contain the Ljungdahl- Wood pathway for acetogenesis (Berraud, C., 2000 "Production of highly concentrated vinegar in fed-batch culture" *Biotechnol. Lett.* 22:451-454; Ljungdahl, L. G., 1986, "The autotrophic pathway of acetate synthesis in acetogenic bacteria" *Ann. Rev. Microbiol.* 40:415-450). Specifically, *Clostridium thermoaceticum* containing the Ljungdahl-Wood pathway produce higher yields of acetate than TC36 (Cheryan, M., S. Parekh, M. Shah and K. Witjitra, 1997 "Production of acetic acid by *Clostridium thermoaceticum*" *Adv. Appl. Microbiol.* 43:1-33). As well, maximum titres with TC36 are lower than can be achieved by ethanol oxidation using *Acetobacter* in the two-step commercial process (Berraud, C., 2000 "Production of highly concentrated vinegar in fed-batch culture" *Biotechnol. Lett.* 22:451-454). However, the specific gene deletions of TC36 lead to acetate production rates almost two-fold higher than either of the aforementioned processes and require only mineral salts as nutrients.

*E. coli* TC36 offers a unique set of advantages over currently employed biocatalysts for the commercial production of acetate: a single step process using sugars as substrates, high rates of acetate production, high acetate yields, simple nutrition (mineral salts medium), and a robust metabolism permitting the bioconversion of hexoses, pentoses, and many dissacharides.

In an alternative embodiment, the subject invention provides a new biocatalyst for the efficient production of pyruvate from glucose that requires only simple mineral salts as nutrients.

As discussed herein, in a preferred embodiment, the materials and methods of the subject invention provide at least the following advantages:

1. The ability to convert hexose and pentose sugars to acetate at very high carbon efficiency in mineral salts medium without the addition of complex nutrients.

2. The lack of plasmids, which may be lost during scale up. This results in a simplified process at less cost.

3. The absence of a need for antibiotic selection. This provides cost and public health advantages.

4. The absence of antibiotic resistance genes. This also provides a public health advantage.

Production of Acetate

Genetically modified *E. coli* W3110 was developed to produce acetic acid as the primary product from glucose during aerobic growth using only mineral salts as nutrients. The resulting biocatalyst (TC36) contains multiple chromosomal alterations (FIG. 1) that direct carbon flow to acetate and minimize carbon loss to cell mass, $CO_2$, and alternative products. Strain TC36 is devoid of plasmids and antibiotic resistance genes, both potential advantages for commercial use. The subject invention provides an additional derivative of *Escherichia coli* W3110 as a new biocatalyst for the production of homo-acetate. Acetate production by this new strain (TC36) approaches the theoretical maximum of two acetate per glucose due to the disruption of oxidative phosphorylation.

Chromosomal deletions were used instead of point mutations to maximize stability. All antibiotic resistance genes and auxotrophic requirements were eliminated to permit growth in simple mineral salts medium. During oxidative metabolism, up to half of the substrate carbon can be converted to roughly equal amounts of cell mass and $CO_2$ (Contiero, J., C. Beatty, S. Kumar, C. L. DeSanti, W. R. Strohl, and A. Wolfe, 2000 "Effects of mutations in acetate metabolism on high-cell-density growth of *Escherichia coli*" *J. Ind. Microbiol.* 24:421-430; Neidhardt, F. C., J. L. Ingraham, and M. Schaechter, 1990 "Physiology of the bacterial cell: A molecular approach" Sinauer Associates, Inc., Sunderland, Mass.; Varma, A., B. W. Boesch, and B. O. Palsson, 1993 "Stoichiometric interpretation of *Escherichia coli* glucose catabolism under various oxygenation rates" *Appl. Environ. Microbiol.* 59:2465-2473) with minimal carbon flow into alternative products, such as acetate.

To reduce the opportunity for excessive growth during oxidative metabolism, ATP production from NADH oxidation (oxidative phosphorylation) can be eliminated (or substantially reduced) by deleting the portion of $(F_1F_0)H^+$-ATP synthase involved in membrane assembly while preserving a functional cytoplasmic $F_1$-ATPase to provide gratuitous hydrolysis of ATP. With this mutation, a maximum of 4 ATP molecules (net) can be produced per glucose (assumes all pyruvate is metabolized to acetyl~CoA and acetate) as compared to a theoretical maximum of 33 ATP molecules for wild-type strains of *E. coli*. Substantial reduction refers to a greater than 80% reduction.

Excessive oxidation of substrate to $CO_2$ and NADH production were eliminated by disrupting the cyclic function of the tricarboxylic acid cycle ($\Delta sucA$) with the added benefit of reducing oxygen demand for NADH oxidation. Additional mutations were introduced to eliminate all major fermentation pathways as alternative routes for NADH oxidation, minimizing the formation of alternative products. The resulting strain, TC36, has absolute requirements for substrate level phosphorylation and for an external electron acceptor that can couple to the electron transport system during growth in mineral salts medium to maintain redox balance. With genetic blocks in all major fermentation pathways and oxidative phosphorylation, this strain is relatively insensitive to variations in dissolved oxygen.

The $(F_1F_0)H^+$-ATP synthase and 2-ketoglutarate dehydrogenase mutations introduced into TC36 to minimize the levels of ATP and NAD(P)H from glucose under oxidative conditions would also be expected to promote glycolysis through native allosteric controls (Neidhardt, F. C., J. L. Ingraham, and M. Schaechter, 1990 "Physiology of the bacterial cell: A molecular approach" Sinauer Associates, Inc., Sunderland, Mass.; Underwood, S. A., M. L. Buszko, K. T. Shanmugam, and L. O. Ingram, 2002 "Flux through citrate synthase limits the growth of ethanologenic *Escherichia coli* KO11 during xylose fermentation" *Appl. Environ. Microbiol.* 68:1071-1081), providing a mechanism for the observed 2-fold increase in glycolytic flux as compared to W3110 (wild type).

With additional mutations in fermentation pathways, further metabolism of pyruvate was limited primarily to small biosynthetic needs and conversion to acetyl~CoA by the pyruvate dehydrogenase complex. Although pyruvate dehydrogenase is activated by low NADH, acetyl~CoA production may be limited by the availability of free CoA (note pyruvate accumulation in TC36 broth between 9 h and 15 h; FIG. 4C). Resulting rises in pyruvate pools would serve as an allosteric activator of phosphotransferase (Suzuki, T., 1969 "Phosphotransacetylase of *Escherichia coli* B, activation by pyruvate and inhibition by NADH and certain nucleotides" *Biochem. Biophys. Acta* 191:559-569), the first committed step for acetate production from acetyl~CoA. Gratuitous ATP hydrolysis by F1-ATPase should ensure the availability of ADP for the final step in acetate production catalyzed by acetate kinase (FIG. 1). Excess pyruvate can also be directly oxidized to acetate by pyruvate oxidase (poxB), an enzyme that is induced during the latter stages of growth and by environmental stress (Chang, Y.-Y., A.-Y. Wang, and J. E. Cronan, Jr., 1994 "Expression of *Escherichia coli* pyruvate oxidase (PoxB) depends on the sigma factor encoded by the rpoS (katF) gene" *Mol. Microbiol.* 11:1019-1028). This enzyme may also contribute to acetate production by TC36.

Eliminating oxidative phosphorylation while preserving $F_1$ ATPase resulted in a 2-fold increase in glycolytic flux (TC24 and TC36).

In a specific embodiment, the subject invention utilizes strategies that delete subunits concerned with the membrane assembly of the $(F_1F_0)H^+$-ATP synthase, create futile cycles for ATP consumption, or increase cytoplasmic levels of the ATPase activities, to decrease cell yield, increase metabolic flux, and increase product yield in bioconversion processes.

Strain TC36 can be used as a biocatalysis platform for the efficient production of oxidized products. Under conditions of glucose excess, strain TC36 produced a maximum of 878 mM acetate, 75% of the maximum theoretical yield or 0.50 g acetate per g glucose. Only cell mass and small amounts of organic acids were produced as co-products with acetate. It is likely that 878 mM acetate approaches the upper limit of tolerance for the metabolism in TC36. Concentrations as low as 50 mM acetate have been shown to induce a stress response in *E. coli* (Kirkpatrick, C., L. M. Maurer, N. E. Oyelakin, Y. N. Yoncheva, R. Maurer, and J. L. Slonczewski, 2001 "Acetate and formate stress: Opposite responses in the proteomes of *Escherichia coli*" *J. Bacteriol.* 183:6466-6477). The minimal inhibitory concentration for growth has been previously reported as 300-400 mM acetate at neutral pH (Lasko, D. R., N. Zamboni, and U. Sauer, 2000 "Bacterial response to acetate challenge: a comparison of tolerance among species" *Appl. Microbiol. Biotechnol.* 54:243-247; Zaldivar, J., and L. O. Ingram, 1999 "Effects of organic acids on the growth and fermentation of ethanologenic *Escherichia coli* LY01" *Biotechnol. Bioengin.* 66:203-210).

Oxygen transfer often becomes limiting during aerobic bioconversion processes, promoting the accumulation of reduced products (Tsai, P. S., M. Nageli, and J. E. Bailey, 2002 "Intracellular expression of *Vitreoscilla* hemoglobin modifies microaerobic *Escherichia coli* metabolism through elevated concentration and specific activity of the cytochrome o" *Biotechnol. Bioeng.* 79:558-567; Varma, A., B. W. Boesch, and B. O. Palsson, 1993 "Stoichiometric interpretation of *Escherichia coli* glucose catabolism under various oxygenation rates" *Appl. Environ. Microbiol.* 59:2465-2473). Synthesis of reduced products was eliminated by mutations in genes (ΔfocApflB ΔfrdCD ΔldhA ΔadhE) encoding the four major fermentation pathways. Excessive oxygen demand and NADH production were also reduced by a deletion in succinate dehydrogenase (sucAΔ). The resulting strain, TC36 (ΔfocApflBΔfrdCD ΔldhA ΔatpFH ΔsucA ΔadhE) metabolizes sugars to acetate with the efficiency of fermentative metabolism, diverting a minimum of carbon to cell mass (biocatalyst) and $CO_2$. By replacing the acetate pathway, a variety of alternative oxidized products can be produced using the mutational strategies employed for the construction of TC36.

Genetically engineered *E. coli* TC36 can produce acetate in a simpler, single step process using glucose and mineral salts with titres and yields equivalent or higher than current batch processes. Although yields for TC36 were lower than those reported for *Clostridium thermoaceticum* which contain the Ljungdahl-Wood Pathway (Cheryan, M., S. Parekh, M. Shah and K. Witjitra, 1997 "Production of acetic acid by *Clostridium thermoaceticum*" *Adv. Appl. Microbiol.* 43:1-33) and maximum titres with TC36 are lower than can be achieved by ethanol oxidation using *Acetobacter* (Berraud, C., 2000 "Production of highly concentrated vinegar in fed-batch culture" *Biotechnol. Lett.* 22:451-454), acetate production rates by TC36 are almost two-fold higher than both and required only mineral salts as nutrients.

*E. coli* TC36 offers a unique set of advantages over currently employed biocatalysts for the commercial production of acetate: a single step process using sugars as substrates, high rates of acetate production, high acetate yields, simple nutrition (mineral salts), and a robust metabolism permitting the bioconversion of hexoses, pentoses, and many dissacharides.

Materials and Methods

Bacterial strains and plasmids. Selected *E. coli* strains and plasmids are listed in Table 1.

TABLE 1

Strains and plasmids.

| Strains & Plasmids | Relevant Characteristics | Reference |
|---|---|---|
| Strains | | |
| W3110 | wild type | ATCC 27325 |
| TOP10F' | lacI$^q$ (episome) | Invitrogen |
| SE2279 | MG1655, pflB ldhA::Tn10 | Laboratory collection (KTS) |
| SZ33 | W3110, ldhA::Tn10 | Described herein |
| SZ40 | W3110, Δ(focA-pflB)::FRT ΔfrdBC | Described herein |
| SZ46 | W3110, Δ(focA-pflB)::FRT ΔfrdBC ldhA::Tn10 | Described herein |
| SZ47 | W3110, Δ(focA-pflB)::FRT ΔfrdBC ΔldhA | Described herein |
| TC20 | W3110, ΔadhE::FRT-tet-FRT | Described herein |
| TC21 | W3110, ΔatpFH::FRT-tet-FRT | Described herein |
| TC23 | W3110, Δ(focA-pflB)::FRT ΔfrdBC ΔldhA Δatp(FH)::FRT-tet-FRT | Described herein |
| TC24 | W3110, Δ(focA-pflB)::FRT ΔfrdBC ΔldhA Δatp(FH)::FRT | Described herein |
| TC25 | W3110, ΔsucA::FRT-tet-FRT | Described herein |
| TC30 | W3110, Δ(focA-pflB)::FRT ΔfrdBC ΔldhA Δatp(FH)::FRT ΔadhE::FRT-tet-FRT | Described herein |
| SE1706 | ΔfrdBC zid::Tn10 | Footnote[1] |
| TC31 | W3110, Δ(focA-pflB)::FRT ΔfrdBC ΔldhA Δatp(FH)::FRT ΔadhE::FRT | Described herein |
| TC32 | W3110, (Succ□), Δ(focA-pflB)::FRT ΔfrdBC ΔldhA Δatp(FH)::FRT ΔadhE::FRT ΔsucA::FRT-tet-FRT | Described herein |

TABLE 1-continued

Strains and plasmids.

| Strains & Plasmids | Relevant Characteristics | Reference |
|---|---|---|
| TC35 | W3110, (Succ+), Δ(focA-pflB)::FRT ΔfrdBC ΔldhA Δatp(FH)::FRT ΔadhE::FRT ΔsucA::FRT-tet-FRT | Described herein |
| TC36 | W3110, (Succ+), Δ(focA-pflB)::FRT ΔfrdBC ΔldhA Δatp(FH)::FRT ΔadhE::FRT ΔsucA::FRT | Described herein |
| Plasmids | | |
| pCR2.1-TOPO | bla kan, TOPO ™ TA cloning vector | Invitrogen |
| pFT-A | bla flp low-copy vector containing recombinase and temperature-conditional pSC101 replicon | Footnote[2] |
| pKD46 | bla γ β exo low-copy vector contaiing red recombinase and temperature-conditional pSC101 replicon | Footnote[3] |
| pLOI2065 | bla, SmaI fragment containing the FRT flanked tet gene | Described herein |
| pLOI2800 | bla kan sucA | Described herein |
| pLOI2801 | bla kan sucA::FRT-tet-FRT | Described herein |
| pLOI2802 | bla kan adhE | Described herein |
| pLOI2803 | bla kan adhE::FRT-tet-FRT | Described herein |
| pLOI2805 | bla kan atpEFH | Described herein |
| pLOI2807 | bla kan atpFH::FRT-tet-FRT | Described herein |

[1]Ohta, K., D. S. Beall, J. P. Mejia, K. T. Shanmugam, and L. O. Ingram (1991) "Genetic improvement of *Escherichia coli* for ethanol production of chromosomal integration of *Zymamonas mobilis* genes encoding pyruvate decarboxylase and alcohol dehydrogenase II. *Appl. Environ. Microbiol.* 57: 893-900.
[2]Posfai, G., M. D. Koob, H. A. Kirkpatrick, and F. C. Blattner. 1997. Versatile insertion plasmids for targeted genome manipulations in bacteria: Isolation, deletion, and rescue of the pathogenicity island LEE of the *Escherichia coli* O157:H7 genome. J. Bacteriol. 179: 4426-4428.
[3]Datsenko, K. A. and B. L. Wanner. 2000. One-step inactivation of chromosomal genes in *Escherichia coli* K-12 using PCR products. Proc. Natl. Acad. Sci. USA 97: 6640-6645.

Working cultures of *E. coli* W3110 (ATCC 27325) derivatives were maintained on a mineral salts medium (per liter: 3.5 g $KH_2PO_4$; 5.0 g $K_2HPO_4$; 3.5 g $(NH_4)_2HPO_4$, 0.25 g $MgSO_4 \cdot 7H_2O$, 15 mg $CaCl_2 \cdot 2H_2O$, 0.5 mg thiamine, and 1 ml of trace metal stock) containing glucose (2% in plates; 3% in broth) and 1.5% agar. The trace metal stock was prepared in 0.1 M HCl (per liter: 1.6 g $FeCl_3$, 0.2 g $CoCl_2 \cdot 6H_2O$, 0.1 g $CuCl_2$, 0.2 g $ZnCl_2 \cdot 4H_2O$, 0.2 g $NaMoO_4$, and 0.05 g $H_3BO_3$). MOPS (0.1 M, pH 7.1) was added to both liquid and solid media (autoclaved separately) when needed for pH control, but was not included in medium used for 10-L fermentations. Minimal medium was also prepared using succinate (1 g $L^{-1}$) and glycerol (1 g $L^{-1}$) as sole sources of carbon (nonfermentable). Succinate (1 g $L^{-1}$) was added as a supplement to glucose-minimal medium when needed. During plasmid and strain construction, cultures were grown in Luria-Bertani (LB) broth or on LB plates (1.5% agar) (Sambrook, J. and D. W. Russell, 2001 "Molecular cloning: A laboratory manual" Cold Spring Harbor Press, Cold Spring Harbor, N.Y.). Glucose (2%) was added to LB medium for all strains containing mutations in $(F_1F_0)H^+$-ATP synthase. Antibiotics were included as appropriate (kanamycin, 50 mg $L^{-1}$; ampicillin, 50 mg $L^{-1}$; and tetracycline, 12.5 or 6.25 mg $L^{-1}$). Fusaric acid plates were used to select for loss of tetracycline resistance.

Genetic methods. Standard methods were used for plasmid construction, phage P1 transduction, electroporation, and polymerase chain reaction (PCR) (Miller, J. H., 1992 "A short course in bacterial genetics: A laboratory manual and handbook for *Escherichia coli* and related bacteria" Cold Spring Harbor Press, Cold Spring Harbor, N.Y.; Sambrook, J. and D. W. Russell, 2001 "Molecular cloning: A laboratory manual" Cold Spring Harbor Press, Cold Spring Harbor, N.Y.). Chromosomal DNA from *E. coli* W3110 (and derivatives) served as a template to amplify genes using primers complementary to coding regions (ORFiners) purchased from the Sigma Scientific Company (St. Louis, Mo.).

PCR products were initially cloned into plasmid vector pCR2.1-TOPO. During plasmid constructions, restriction products were converted to blunt ends using either the Klenow fragment of DNA polymerase (5' overhang) or T4 DNA polymerase (3' overhang) as needed. Integration of linear DNA was facilitated by using pKD46 (temperature conditional) containing an arabinose-inducible red recombinase (Datsenko, K. A. and B. L. Wanner, 2000 "One-step inactivation of chromosomal genes in *Escherichia coli* K-12 using PCR products" *Proc. Natl. Acad. Sci. USA* 97:6640-6645). Integrants were selected for tetracycline resistance (6.25 mg $L^{-1}$) and screened for appropriate antibiotic resistance markers and phenotypic traits. At each step, mutations were verified by analyses of PCR products and fermentation products. FRT-flanked antibiotic resistance genes used for selection were deleted using a temperature-conditional plasmid (pFT-A) expressing FLP recombinase from a chlortetracycline-inducible promoter (Martinez-Morales, F., A. G. Borges, A. Martinez, K. T. Shanmugam, and L. O. Ingram, 1999 "Chromosomal integration of heterologous DNA in *Escherichia coli* with precise removal of markers and replicons during construction" *J. Bacteriol.* 181:7143-7148; Posfai, G., M. D. Koob, H. A. Kirkpatrick, and F. C. Blattner, 1997 "Versatile insertion plasmids for targeted genome manipulations in bacteria: Isolation, deletion, and rescue of the pathogenicity island LEE of the *Escherichia coli* 0157:1-17 genome" *J. Bacteriol.* 179:4426-4428).

A removable tetracycline cassette (FRT-tet-FRT) was constructed (pLOI2065) which is analogous to the kanamycin cassette (FRT-kan-FRT) in pKD4 (Datsenko, K. A. and B. L. Wanner, 2000 "One-step inactivation of chromosomal genes in *Escherichia coli* K-12 using PCR products" *Proc. Natl. Acad. Sci. USA* 97:6640-6645). In both cassettes, flanking FRT sites are oriented in the same direction to allow efficient in vivo excision by FLP recombinanase (Posfai, G., M. D. Koob, H. A. Kirkpatrick, amd F. C. Blattner, 1997 "Versatile insertion plasmids for targeted genome manipulations in bacteria: Isolation, deletion, and rescue of the pathogenicity island LEE of the *Escherichia coli* O157:H7 genome" *J. Bacteriol.* 179:4426-4428). Plasmid pLOI2065 contains two EcoRI sites and two SmaI sites for isolation of the FRT-tet-FRT cassette. The sequence for pLOI2065 has been deposited in GenBank (Accession No. AF521666).

Deletion of adhE. To construct an adhE mutant, the coding region (2.68 kbp) was amplified by PCR and cloned into pCR2.1-TOPO. The central region of adhE (1.06 kbp) was deleted using HincII (2 sites) and replaced with a 1.7 kbp SmaI fragment from pLOI2065 containing the FRT-tet-FRT cassette to produce pLOI2803. This plasmid was linearized by digestion with PvuI and ScaI, and served as a template to amplify (adhE primers) the 3.17 kbp region containing adhE::FRT-tet-FRT. Amplified DNA was purified and introduced into W3110 by electroporation. Recombinants from double crossover events were identified by antibiotic markers, confirmed by analysis of PCR and fermentation products. One clone was selected and designated TC20.

P1 transduction was used to transfer a mutation (frdBC zid::Tn10) from SE1706 into SZ32, designated SZ35(ΔfocA-pflB::FRT ΔfrdBC zid::Tn10). The tet gene was removed from SZ35 by fusaric acid selection to produce SZ40(ΔfocA-pflB:FRT ΔfrdBC).

Deletion of pflB. A focA-pflB::FRT mutation was constructed using the method of Datsenko and Wanner (Datsenko, K. A. and B. L. Wanner, 2000 "One-step inactivation of chromosomal genes in *Escherichia coli* K-12 using PCR products" *Proc. Natl. Acad. Sci. USA* 97:6640-6645). Hybrid primers were designed which are complementary to *E. coli* chromosomal genes and to the antibiotic cassette (FRT-kan-FRT) in pKD4. The sense primer (TTACTCCGTATTTG-CATAAAAA-CCATGCGAGTTACGGGCCTATAA GTGTAGGCTGGAGCTGCTTC) (SEQ ID NO:1) consisted of an initial 45 bp (bold) corresponding to the −130 to −85 region of foc followed by 20 bp (underlined) corresponding to the primer 1 region of pKD4. The antisense primer TAGAT-TGAGTGAAGGTACGAGTAATAACGTCCTGCTGC-TGTTCTCATATGAATATCCTCCTTAG) (SEQ ID NO:2) consisted of an initial 45 bp (bold) of the C-terminal end of pflB followed by 20 bp (underlined) corresponding to primer 2 region of pKD4. The FRT-kan-FRT cassette was amplified by PCR using these primers and pKD4 as the template. After purification, amplified DNA was electroporated into *E. coli* BW25113 (pKD46). The resulting kanamycin-resistant recombinant, pAH218, contained FRT-kan-FRT in the deleted region of pflB (46 bp remaining). A phage P1 lysate prepared from AH218 (pflB::FRT-kan-FRT) was used to transfer this mutation into W3110 to produce strain SZ31 (pflB::FRT-kan-FRT). After verifying this mutation by analyses of PCR products, fermentation products, and antibiotic markers, the kan gene was removed from the chromosome by FLP recombinase using a temperature-conditional helper plasmid (pFT-A). After removal of helper plasmid by growth at 42° C., the resulting kanomycin-sensitive strain (focA-pflB::FRT) was designated SZ32.

Deletion of focA-pf/B:FRT, frdBC, ldhA. The ldhA::Tn10 mutation in *E. coli* SE2279 was transduced into *E. coli* W3110 using phage P1 to produce strain SZ33. P1 phage grown on SZ33 was used to transfer this mutation into SZ40 (Δ(focA-pflB)::FRT ΔfrdCD) to produce SZ46. Tetracycline-sensitive derivatives of SZ46 were selected using fusaric acid medium. One clone was designated SZ47 (Δ(focA-pflB)::FRT ΔfrdBC ΔldhA). The ΔldhA mutation in SZ47 was confirmed by the absence of lactate in fermentation broth, an inability to grow anaerobically in glucose-minimal media, and by PCR analysis using ldhA ORFiners (1.0 kbp for the wild type ldhA as compared to 1.1 kbp for SZ47). The slightly larger size of the amplified product from SZ47 is attributed to remnants of Tn10.

Figure 2:
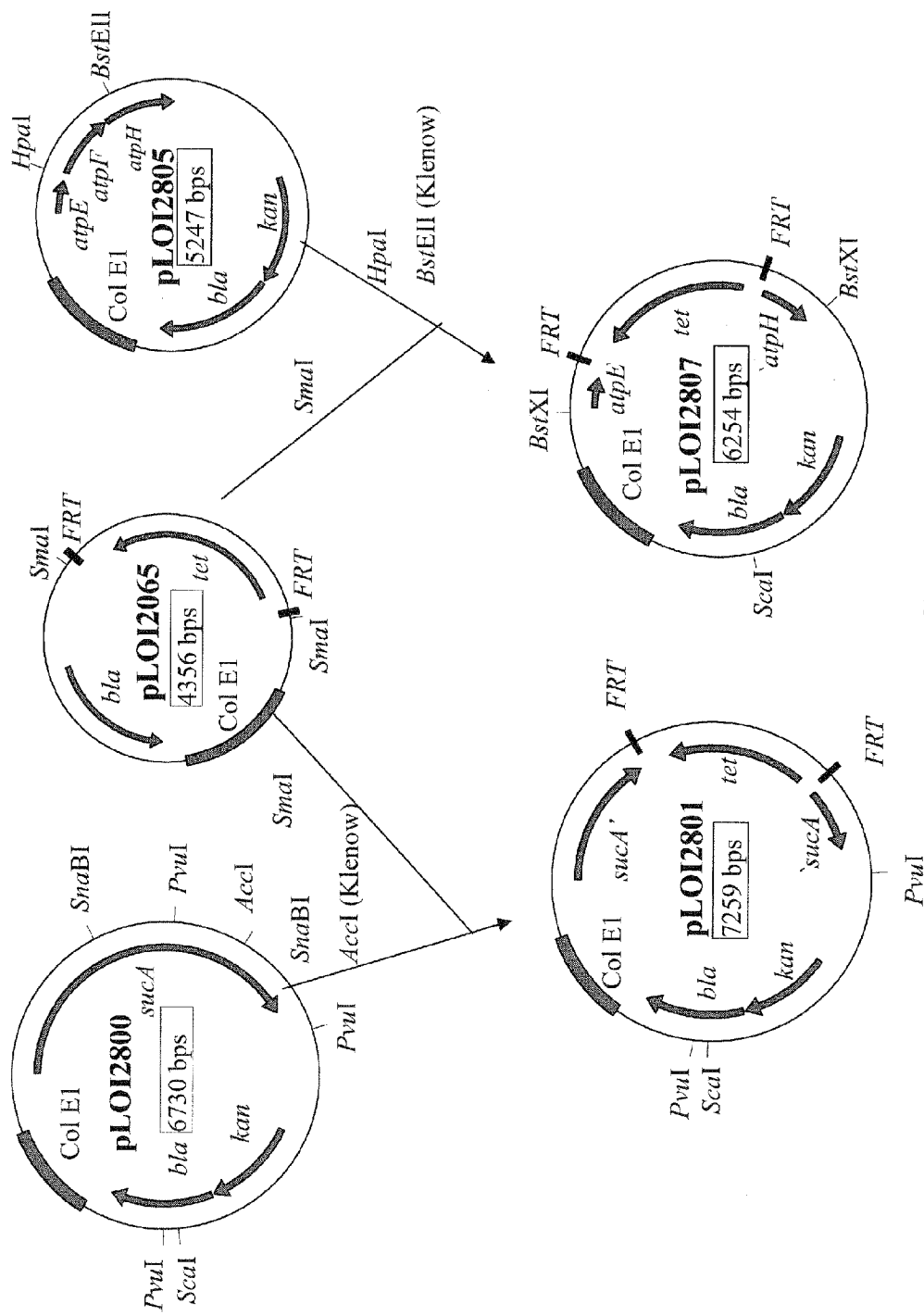
FIG. 2 Diagram summarizing plasmid constructions.

Deletion of atpFH. The atpEFH coding region of the atpIBEFHAGDC operon was amplified by PCR using primers (ORFiners, Sigma Scientific, St. Louis, Mo.) complementary to the 5'-end of the atpE gene and the 3'-end of the atpH. The amplified fragment (1.3 kbp) was cloned into pCR2.1-TOPO and one clone selected in which the atpEFH genes were oriented to permit expression from the lac promoter (pLOI2805; FIG. 2). The atpF gene and 117 nucleotides at the 5' end of atpH gene were removed from pLOI2805 by digestion with HpaI and BstEII (Klenow-treated). This region was replaced with a 1.7 kbp SmaI fragment from pLOI2065 containing the FRT-tet-FRT cassette to produce pLOI2807 (FIG. 2). After digestion with ScaI, pLOI2807 served as a template for amplification of the atpEΔ(FH)::FRT-tet-FRT region (2.4 kbp) using the 5' atpE and 3' atpH primers. Amplified DNA was precipitated, digested again with ScaI to disrupt any residual plasmid, and purified by phenol extraction. This DNA was introduced into *E. coli* W3110(pKD46) by electroporation while expressing red recombinase. Plasmid pKD46 was eliminated by growth at 42° C. Recombinants (double cross-over) were identified using antibiotic markers (tetracycline resistant; sensitive to ampicillin and kanamycin) and by the inability to grow on succinate-minimal plates or glycerol-minimal plates in the absence of glucose (fermentable carbon source). Integration was further confirmed by PCR analysis using the 5' atpE primer and the 3' atpH primer (1.3 kbp fragment for W3110; 2.3 kbp fragment for mutants). One clone was selected and designated TC21(Δatp(FH)::FRT-tet-FRT).

Phage P1 was used to transduce the Δatp(FH)::FRT-tet-FRT mutation in TC21 to SZ47 and produce TC23. The tet gene was removed from TC23 by the FLP recombinase (pFT-A). After elimination of pFT-A by growth at 42° C., the Δatp(FH)::FRT mutation was further confirmed by PCR analysis using the 5' atpE primer and the 3' atpH primer (0.8 kbp for deletion and 1.3 kbp for SZ47). The resulting strain was designated TC24(ΔfocA-pflB::FRT ΔfrdBC ΔldhA ΔalpFH::FRT).

Deletion of adhE. Phage P1 was used to transduce the ΔadhE::FRT-tet-FRT mutation in TC20 to TC24 and produce TC30. Chromosomal integration was confirmed by PCR analysis using adhE primers (2.7 kbp for TC24 and 3.2 kbp for the ΔadhE::FRT-tet-FRT mutant). The tet gene was deleted from TC30 by FLP recombinase using pFT-A. After elimination of pFT-A by growth at 42° C., a clone was selected and designated TC31(Δ(focA-pflB)::FRT ΔfrdBC ΔldhA Δatp(FH)::FRT ΔadhE::FRT).

Deletion of part of sucA. The sucA coding region was amplified using ORFiners. The resulting 2.8 kbp PCR product was cloned into pCR2.1-TOPO to produce pLOI2800 (FIG. 2) in which the sucA coding region was oriented to permit expression from the lac promoter. A 1.1 kbp fragment was removed from central region of sucA by digestion of pLOI2800 with SnaBI and AccI (Klenow-treated). This region was replaced with a 1.7 kbp SmaI fragment containing the FRT-tet-FRT cassette from pLOI2065 to produce pLOI2801 (FIG. 2). Plasmid pLOI2801 was digested with PvuI and ScaI and used as a template to amplify the 3.3 kbp region containing sucA::FRT-tet-FRT using sucA ORFiners. Amplified DNA was precipitated, digested with PvuI and ScaI to disrupt any residual circular plasmid, and extracted with phenol. Purified DNA was electroporated into *E. coli* W3110(pKD46) while expressing red recombinase. Plasmid pKD46 was eliminated by growth at 42° C. Disruption of sucA was confirmed by PCR analysis using sucA ORFiners (2.8 kbp fragment for wild type and 3.3 kbp for sucA::FRT-tet-FRT mutants) and designated TC25.

Phage P1 was used to transduce the sucA::FRT-tet-FRT mutation from TC25 into TC31. Transfer was verified by PCR analysis (2.8 kbp for wild type sucA and 3.3 kbp for sucA:: FRT-tet-FRT mutants) and phenotype (succ). Inactivation of 2-ketoglutarate dehydrogenase (ΔsucA) in this ΔfrdBC background resulted in an undesirable auxotrophic requirement for succinate ($Succ^-$) during growth on glucose-minimal medium. The resulting strain was designated TC32($Succ^-$, Δ(focA-pflB)::FRT ΔfrdBC ΔldhA Δatp(FH)::FRT ΔadhE:: FRT ΔsucA::FRT-tet-FRT).

Elimination of $Succ^-$ mutants. Spontaneous $Succ^+$ mutants of TC32 were readily obtained after serial transfers in glucose-minimal broth containing decreasing amounts of succinate (4 mM to 0.4 mM) followed by selection on glucose-minimal plates without succinate. Over 170 clones were recovered per ml of culture after enrichment, approximately 3% of viable cells. Ten clones were tested and all grew well in glucose minimal broth without succinate and produced acetate as the dominant product. One was selected (TC35) for deletion of the tet gene using the FLP recombinase. This deletion was confirmed by analysis of PCR products using sucA primers (3.3 kbp for TC35 and 1.8 kbp after tet deletion). The resulting strain was designated TC36 ($Succ^+$, Δ(focA-pflB)::FRT ΔfrdBC ΔldhA Δatp(FH)::FRT ΔadhE:: FRT ΔsucA::FRT).

Total ATPase activity was examined in disrupted cell extracts of TC36 and W3110 (wild type). The activity in TC36 (0.355 U $mg^{-1}$ protein) was equivalent to 71% of the unmodified parent (0.502 U $mg^{-1}$ protein), confirming that $F_1$-ATPase was not inactivated by the ΔatpFH::FRT mutation. This is similar to the levels of ATPase reported for an atpH mutant of *E. coli* which blocked membrane assembly and coupling to oxidative phosphorylation (Sorgen, P. L., T. L. Caviston, R. C. Perry, and B. D. Cain, 1998 "Deletions in the second stalk of F1F0-ATP synthase in *Escherichia coli*" *J. Biol. Chem.* 273:27873-27878).

Fermentation. Acetate production was examined in glucose-minimal medium containing 167 mM glucose using a New Brunswick Bioflow 3000 fermentor with a 10 L working volume (37° C., dual Rushton impellers, 450 rpm). Dissolved oxygen was maintained at 5% of air saturation (unless otherwise stated) by altering the proportion of $N_2$ and $O_2$. Broth was maintained at pH 7.0 by the automatic addition of 11.4 M KOH. For fed batch experiments, additional glucose was added from a sterile 60% stock. Three fed batch regimes were investigated: A. 3% glucose initially with the addition of 3% after 12 h (6% total); B. 6% glucose initially with the addition of 4% glucose after 16 h (10% total); C. 3% glucose initially with multiple additions to maintain glucose levels above 100 mM.

Seed cultures were prepared by inoculating colonies from a fresh plate (48 h) into 3 ml of glucose-minimal medium (13×100 mm tube) containing 0.1 M MOPS. After incubation for 14 h (120 rpm rotator), cultures were diluted 400-fold into 1-L baffled flask containing 200 ml of mineral salts medium (37° C., 280 rpm). When cells reached 1.5-2.2 $OD_{550nm}$, sufficient culture volume was harvested (5000 rpm, 25° C.) to provide an inoculum of 33 mg dry cell weight $L^{-1}$ in the 10-L working volume.

Broth samples were removed to measure organic acids, residual glucose, and cell mass. Volumetric and specific rates were estimated from measured values for glucose and acetate using Prism software (GraphPad Software, San Diego, Calif.). A smooth curve was generated with 10 points per min (Lowess method) to fit measured results. The first derivative (acetate or glucose versus time) of each curve served as an estimate of volumetric rate. Specific rates (mmoles $L^{-1}$ $h^{-1}$ $mg^{-1}$ dry cell weight) were calculated by dividing volumetric rates by respective values for cell mass.

ATPase. Cells were grown for enzyme assays as described above for seed cultures. Upon reaching 0.75-1.0 $OD_{550nm}$, cultures were chilled on ice and harvested by centrifugation (8000×g, 5 mM at 4° C.). Cell pellets were washed 5 times with 0.1 M Tris-HCl (pH 7.55), resuspended in 1 ml of this buffer, and broken using a model W220F ultrasonic cell disruptor (Heat Systems Ultrasonics, Plainview, N.Y., USA). Total ATPase activity in disrupted cell preparations was assayed at pH 7.55 essentially as described by Evans (Evans, D. J., Jr., 1969 "Membrane adenosine triphosphate of *Escherichia coli*: activation by calcium ion and inhibition by cations" *J. Bacteriol.* 100:914-922). Inorganic phosphate was measured by the method of Rathbun and Betlach (Rathbun, W. B., and M. V. Betlach, 1969 "Estimation of enzymatically produced orthophosphate in the presence of cysteine and adenosine triphosphate" *Anal. Biochem.* 20:436-445). Results represent an average for three cultures of each strain Specific activity is expressed as μmmol $P_i$ released $min^{-1}$ $mg^{-1}$ protein.

Total ATPase activity was examined in disrupted cell extracts of TC36 and W3110 (wild type). The activity in TC36 (0.355 U $mg^{-1}$ protein) was equivalent to 71% of the unmodified parent (0.502 U $mg^{-1}$ protein), confirming that $F_1$-ATPase was not inactivated by the ΔatpFH::FRT mutation. This is similar to the levels of ATPase reported for an atpH mutant of *E. coli* which blocked membrane assembly and coupling to oxidative phosphorylation (Sorgen, P. L., T. L. Caviston, R. C. Perry, and B. D. Cain, 1998 "Deletions in the second stalk of F1F0-ATP synthase in *Escherichia coli*" *J. Biol. Chem.* 273:27873-27878).

Analyses. Organic acids and glucose concentrations were determined using a Hewlett Packard HPLC (HP 1090 series II) equipped with a UV monitor (210 nm) and RI detector. Products were separated using a Bio-Rad HPX 87H column (10 μl injection) with 4 mM $H_2SO_4$ as the mobile phase (0.4 ml $min^{-1}$, 45° C.). Cell mass was estimated by measuring $OD_{550nm}$ (1.0 $OD_{550nm}$ is equivalent to 0.33 g $L^{-1}$ dry cell weight) using a Bausch & Lomb Spectronic 70 spectrophotometer with 10×75 mm culture tubes as cuvettes. Protein concentration was determined using the BCA Protein Assay Kit from Pierce (Rockford, Ill.).

Following are examples which illustrate procedures for practicing the invention. These examples should not be construed as limiting. All percentages are by weight and all solvent mixture proportions are by volume unless otherwise noted.

EXAMPLE 1

Construction of a Homo-Acetate Fermentation Pathway in *E. coli* W3110

Fermentation of sugars through native pathways in *E. coli* produces a mixture of organic acids, ethanol, $CO_2$ and $H_2$ (FIG. 1). Acetate and ethanol are typically produced in approximately equimolar amounts from acetyl~CoA to provide redox balance (Clark, D. P., 1989 "The fermentation pathways of *Escherichia coli*. FEMS"*Microbial. Rev.* 63:223-234; de Graef, M. R., S. Alexeeva, J. L. Snoep, and M.

J. Teixiera de Mattos, 1999 "The steady-state internal redox state (NADH/NAD) reflects the external redox state and is correlated with catabolic adaptation in *Escherichia coli*" *J. Bacterial.* 181:2351-2357). To construct a strain for homoacetate production, removable antibiotic resistance genes were used to sequentially inactivate chromosomal genes encoding alternative pathways.

Inspection of native pathways in *E. coli* (FIG. 1) indicated that the production of acetate and $CO_2$ as sole metabolic products from glucose will require an external electron acceptor such as oxygen. Due to low oxygen solubility, however, it is difficult to satisfy the oxygen demand from active *E. coli* metabolism and a portion of substrate is typically converted to fermentation products such as lactate and ethanol. This problem was eliminated by combining deletions in genes encoding lactate dehydrogenase, pyruvate formatelyase, and alcohol/aldehyde dehydrogenase.

A deletion was inserted into the pflB gene, the ldhA gene, and the adhE gene of W3110. These mutations eliminated the production of $CO_2$, lactate, and ethanol in 3% glucose-minimal media (Table 2).

nase and succinyl coenzyme A synthetase: roles of ArcA, Fnr, and the upstream sdhCDAB promoter" *J. Bacteriol.* 179: 4138-4142), disrupting the cyclic function of the TCA cycle. Deleting part of the sucA gene imposed a restriction in carbon flow through the TCA cycle.

Again, growth under oxidative conditions is characterized by conversion of up to 50% of substrate carbon to cell mass (Neidhardt, F. C., J. L. Ingraham, and M. Schaechter, 1990 "Physiology of the bacterial cell: A molecular approach" Sinauer Associates, Inc., Sunderland, Mass.). To reduce the potential drain of substrate into cell mass, a mutation was introduced into SZ47 that deleted portions of two subunits in $(F_1F_0)H^+$-ATP synthase concerned with assembly to the plasma membrane (Sorgen, P. L., T. L. Caviston, R. C. Perry, and B. D. Cain, 1998 "Deletions in the second stalk of F1F0-ATP synthase in *Escherichia coli*" *J. Biol. Chem.* 273:27873-27878), disrupting oxidative phosphorylation while preserving the hydrolytic activity of $F_1$-ATPase in the cytoplasm. Thus, the strain is able to grow in minimal medium without a fermentable carbon source (substrate level phosphorylation) and retains the ability to oxidize NADH by the electron transport system.

TABLE 2

Comparison of metabolic rates.

| Strain | Specific Growth Rate (μ) | Max Vol[a] Glucose Utilization (mmol liter$^{-1}$ h$^{-1}$) | Max Spec Glucose[b] Utilization (mmol h$^{-1}$ g$^{-1}$) | Max Vol[a] Acetate Production (mmol liter$^{-1}$ h$^{-1}$) | Max Spec[b] Acetate Production (mmol h$^{-1}$ g$^{-1}$) |
|---|---|---|---|---|---|
| W3110 | 0.87 | 18 | 9 | 9.5 | 10 |
| SZ47 | 0.87 | 22 | 11 | 9 | 10 |
| TC24 | 0.78 | 28 | 20 | 26 | 16 |
| TC36 | 0.69 | 33 | 18 | 23 | 16 |

[a]Maximum volumetric rates for glucose utilization and acetate production.
[b]Maximim specific rates (dry cell weight basis) for glucose utilization and acetate production. Values for glucose represents a measure of maximal glycolytic flux.

Several different mutations can be used to block succinate production (FIG. 1). During fermentation, the tricarboxylic acid (TCA) pathway serves primarily as a source of carbon skeletons for biosynthesis. Previous experience with *E. coli* B strains (Ingram, L. 0., H. C. Aldrich, A. C. C. Borges, T. B. Causey, A. Martinez, F. Morales, A. Saleh, S. A. Underwood, L. P. Yomano, S. W. York, J. Zaldivar, and S. Zhou, 1999 "Enteric bacterial catalysts for fuel ethanol production." *Biotechnol. Prog.* 15:855-866) engineered for ethanol production has shown that a deletion in the frdABCD operon can be used as an alternative method to block succinate production by preventing the production of fumarate reductase. Thus, the deletion of the frdCD gene eliminates the production of succinate by reductive reactions.

The TCA cycle was further disrupted by the deletion of sucA (FIG. 1) During oxidative growth, up to 50% of substrate carbon can be lost as $CO_2$ (Neidhardt, F. C., J. L. Ingraham, and M. Schaechter, 1990 "Physiology of the bacterial cell: A molecular approach" Sinauer Associates, Inc., Sunderland, Mass.). This loss of carbon can be attributed in large measure to the high efficiency of the TCA cycle and the electron transport system (NADH oxidation). During fermentative metabolism, the production of $CO_2$ and NADH are reduced primarily by strong repression of sucAB encoding 2-ketoglutarate dehydrogenase (Cunningham, L. and J. R. Guest, 1998 "Transcription and transcript processing in the sdhCDAB-sucABCD operon of *Escherichia coli*" *Microbiology* 144:2113-2123; Park, S.-J., G. Chao, and R. P. Gunsalus, 1997 "Aerobic regulation of the sucABCD gene of *Escherichia coli*, which encode α-ketoglutarate dehydroge- These deletions resulted in strain TC32, which required succinate for growth on glucose-minimal medium. Thus, spontaneous Succ$^+$ mutants of TC32 were obtained by performing serial transfers in glucose-minimal broth containing decreasing amounts of succinate followed by selection on glucose-minimal plates without succinate.

The resulting strain, TC36 has absolute requirements for a fermentable carbon source (substrate level phosphylation) and for an external electron acceptor that can couple to the electron transport system during growth in mineral salts medium to maintain redox balance. With genetic blocks in all major fermentation pathways and oxidative phosphorylation, this strain is relatively insensitive to variations in dissolved oxygen. TC36(ΔfocApflB ΔfrdCD ΔldhA ΔatpFH ΔsucA ΔadhE) metabolizes sugars to acetate with the efficiency of fermentative metabolism, diverting a minimum of carbon to cell mass (biocatalyst) and $CO_2$. By replacing the acetate pathway, a variety of alternative oxidized products can be produced using the mutational strategies employed for the construction of TC36.

EXAMPLE 2

Effects of Gene Disruptions on Growth and Glycolytic Flux

TC36 was genetically engineered for the production of acetate from carbohydrates such as glucose. Batch fermentations with pH control were used to compare the performance of this strain with W3110 (wild type) and two intermediate strains used for construction, SZ47(ΔpflB,ΔfrdCD,ΔldhA) and TC24(ΔpflB,ΔfrdCD,ΔldhA ΔatpFH). Under 5% oxygen saturation and 3% glucose (37° C.) test conditions, the broth pH was maintained at neutrality to minimize toxicity from undissociated acids (Chotani, G., T. Dodge, A. Hsu, M. Kumar, R. LaDuca, D. Trimbur, W. Weyler, and K. Sanford, 2000 "The commercial production of chemicals using pathway engineering" Biochim. Biophys. Acta 1543:434-455).

Figure 3A:
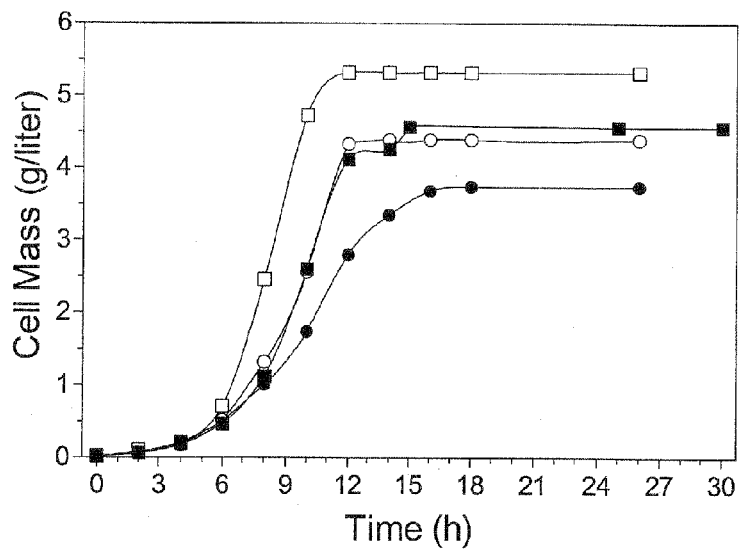
FIGS. 3A-3C Effects of selected mutations on growth (A), glucose utilization (B), and base consumption (C). Symbols: ■, W3110 (wild type); □, SZ47(Δ(focA-pflB)::FRT ΔfrdBC ΔldhA); ○, TC24(Δ(focA-pflB)::FRT ΔfrdBC ΔldhA Δatp(FH)::FRT); ●, TC36 (succ$^+$; Δ(focA-pflB)::FRT ΔfrdBC ΔldhA Δatp(FH)::FRT ΔadhE::FRT ΔsucA::FRT).

Disruption of oxidative phosphorylation and the cyclic function of the tricarboxylic acid cycle, elimination of the primary fermentation pathways, and the production of acetate as the primary end-product from glycolysis had relatively little effect on the growth of E. coli. The maximum growth rates for strains W3110 (wild type) and SZ47 (lacking the three native fermentation pathways) were similar although the cell yield for SZ47 was higher (FIG. 3A; Table 2 and Table 3). Inactivation of oxidative phosphorylation (ΔatpFH) resulted in a small reduction in growth rate and cell yield (TC24). Cell yield and growth rate were lowest for strain TC36 containing additional mutations in 2-ketoglutarate dehydrogenase (ΔsucA) and alcohol dehydrogenase (ΔadhE), approximately 80% of the unmodified parent W3110.

Figure 3B:
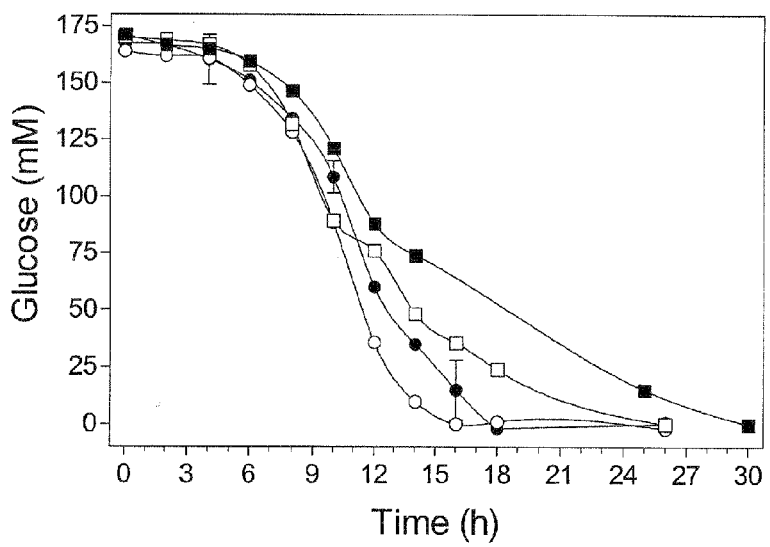

Maximal rates for glucose utilization (specific and volumetric) were higher for TC36 and TC24 than for W3110 and SZ47 (Table 2). This increase in metabolic activity can be primarily attributed to the ΔatpFH mutation. ATP levels serve as an allosteric regulator of several key glycolytic enzymes (Neidhardt, F. C., J. L. Ingraham, and M. Schaechter, 1990 "Physiology of the bacterial cell: A molecular approach" Sinauer Associates, Inc., Sunderland, Mass.), and acetate kinase (Suzuki, T., 1969 "Phosphotransacetylase of Escherichia coli B, activation by pyruvate and inhibition by NADH and certain nucleotides" Biochim. Biophys. Acta 191:559-569). Differences between strains were particularly evident when comparing incubation times required to complete sugar metabolism (FIG. 3B). With TC36 and TC24, glucose was exhausted in 16-18 h as compared to 26 h for SZ47 and 30 h for W3110. The maximum specific rate of glucose utilization (glycolytic flux) was 9 mmole $h^{-1}$ $g^1$ dry cell weight in the unmodified parent (W3110), 20 mmole $h^{-1}$ $g^{-1}$ dry cell weight in TC24, and 18 mmole $g^{-1}$ dry cell weight in TC36. The slightly lower glycolytic flux in TC36 as compared to TC24 may be related to the increase in ATP yield resulting from improvements in acetate yield (1 ATP per acetate). Assuming protein represents 55% of dry cell weight, maximal glycolytic flux in TC36 is approximately 0.55 μmoles glucose $min^{-1}$ $mg^{-1}$ protein.

The $(F_1F_0)H^+$-ATP synthase and 2-ketoglutarate dehydrogenase mutations introduced into TC36 to minimize the levels of ATP and NAD(P)H from glucose under oxidative conditions also promote glycolysis through native allosteric controls (Neidhardt, F. C., J. L. Ingraham, and M. Schaechter, 1990 "Physiology of the bacterial cell: A molecular approach" Sinauer Associates, Inc., Sunderland, Mass.; Underwood, S. A., M. L. Buszko, K. T. Shanmugam, and L. O. Ingram, 2002 "Flux through citrate synthase limits the growth of ethanologenic Escherichia coli KO11 during xylose fermentation" Appl. Environ. Microbiol. 68:1071-1081), providing a mechanism for the observed 2-fold increase in glycolytic flux as compared to W3110 (wild type).

EXAMPLE 3

Production of Other Organic Acids

A substantial portion of glucose carbon was not recovered in the carbon balance (Table 3) for W3110 (40%) and SZ47 (80%). This loss is attributed to the production of volatile products by high flux through the tricarboxylic acid cycle ($CO_2$) but may also include the reduction of acetyl~CoA to acetaldehyde and ethanol (FIG. 1).

TABLE 3

Summary of fermentation products.

| Strain | Conditions | Cell Yield (g/liter) | Fermentation Products[a] (mM) | | | | | | Yield[b] (%) | Carbon Recovery[c] (% substrate C) |
| --- | --- | --- | --- | --- | --- | --- | --- | --- | --- | --- |
| | | | Acetate | 2-ketoglutarate | Fumarate | Lactate | Pyruvate | Succinate | | |
| W3110 | 3% glucose 5% DO | 4.5 | 30 | 39 | 0.8 | 33 | <1 | 5 | 9 | 60 |
| SZ47 | 3% glucose 5% DO | 5.3 | 6 | 11 | 0.9 | <1 | 1 | 3 | 2 | 20 |
| TC24 | 3% glucose 5% DO | 4.4 | 156 | 1 | 1.0 | <1 | <1 | 2 | 47 | 66 |
| TC36 | 3% glucose 5% DO | 3.5 – 0.2 | 224 – 14 | 16 – 6 | 0.4 – 0.1 | <1 | 0 – 0.5 | 4 – 1 | 68 | 89 |
| TC 36 | 3% glucose 15% DO | 3.2 | 190 | 24 | <1 | <1 | <1 | 3 | 57 | 88 |
| TC36 | 3% Glucose 5% DO N-limited | 2.5 | 220 | 31 | <1 | <1 | <1 | 10 | 66 | 95 |
| TC36 | 3 + 3% glucose 5% DO | 3.8 | 523 | 21 | <1 | 3 | 14 | 2 | 78 | 95 |
| TC36 | 3 + 3% glucose 5% DO N-limited | 3.0 | 572 | 33 | <1 | <1 | <1 | 6 | 86 | 102 |
| TC36 | 6% glucose 5% DO | 4.18 | 415 | 47 | 0.3 | <1 | 46 | 7 | 62 | 92 |
| TC36 | 6 + 4% glucose[d] 5% DO | 4.5 | 767 | 37 | 0.5 | <1 | 72 | 5 | 72 | 97 |

TABLE 3-continued

Summary of fermentation products.

| Strain | Conditions | Cell Yield (g/liter) | Fermentation Products[a] (mM) | | | | | | Yield[b] (%) | Carbon Recovery[c] (% substrate C) |
|---|---|---|---|---|---|---|---|---|---|---|
| | | | Acetate | 2-ketoglutarate | Fumarate | Lactate | Pyruvate | Succinate | | |
| TC36 | Fed batch[e] 5% DO | 4.1 | 878 | 33 | 3.4 | <1 | <1 | 25 | 75 | 88 |

[a]Concentrations in broth after all glucose had been depleted, except as noted.
[b]Yield expressed as a percentage of the maximal theoretical yield (0.67 g acetate per g glucose).
[c]Carbon recovery represents the percentage of substrate carbon recovered. Recovered carbon was calculated as the sum of carbon in cell mass, fermentation products, and CO2.
[d]In the final sample, 44 mM glucose was present.
[e]Excess glucose (9.5%) was added to fermentation to maintain levels above 100 mM; 107 mM glucose was present in the final sample.

Although ethanol was absent in broth samples from all pH-controlled fermentations (sparged at 1 L min$^{-1}$), a small amount of ethanol (6 mM) was found in seed cultures of W3110 (shaken flasks). No ethanol was present in seed cultures of TC36, because of the mutation in alcohol dehydrogenase E (adhE). In W3110, the electron transport system (5% dissolved oxygen) and native fermentation pathways (Table 3) serve as complementary routes for NADH oxidation.

Eliminating the fermentation pathways to produce the strain SZ47, doubled the loss of carbon as volatile products (Table 3) through the TCA cycle. While SZ47 cell yield increased, the rate of acetate production in comparison to W3110 decreased (Table 2 and Table 3).

Figure 4A:
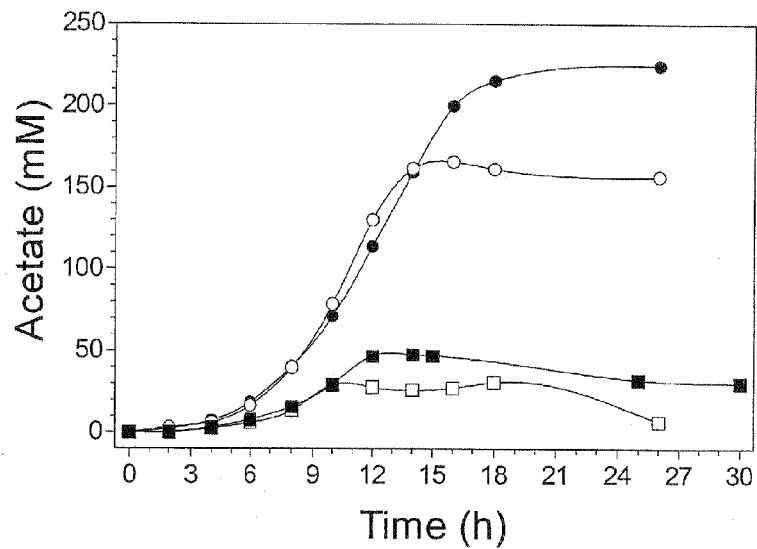
FIGS. 4A-4C Effects of selected mutations on the production of acetate (A), dicarboxylic acids (B), and pyruvate (C). Symbols: ■, W3110 (wild type); □, SZ47(Δ(focA-pflB)::FRT ΔfrdBC ΔldhA); ○, TC24(Δ(focA-pflB)::FRT ΔfrdBC ΔldhA Δatp(FH)::FRT); ●, TC36 (Succ$^+$; Δ(focA-pflB)::FRT ΔfrdBC ΔldhA Δatp(FH)::FRT ΔadhE::FRT ΔsucA::FRT).
Figure 4B:
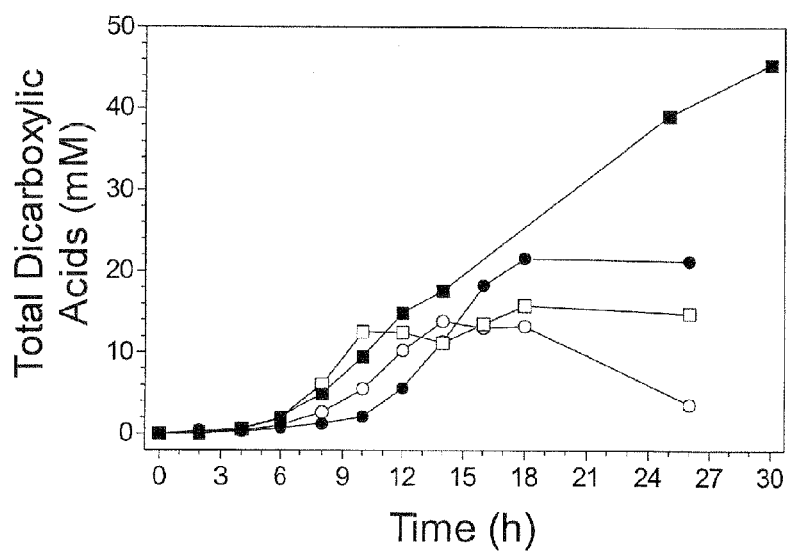
Figure 4C:
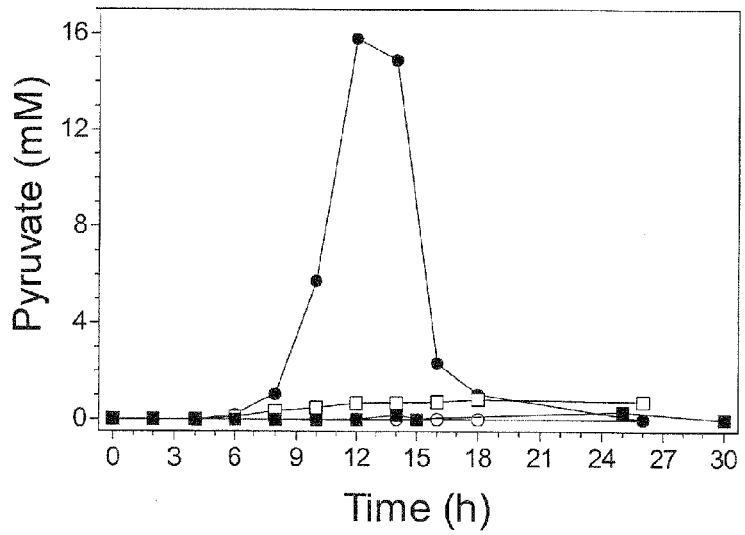

Strain W3110 accumulated the highest levels of dicarboxylic acids (primarily succinate and 2-ketoglutarate produced through the TCA cycle) during glucose metabolism, approximately 3-fold that of the engineered strains (FIG. 4B). The order of appearance of dicarboxylic acids in the broth correlated with growth rate and the order in which each strain entered into stationary phase. Dicarboxylic acids were partially consumed as glucose levels declined, and may represent spillover products from excessive glycolysis during the transition from exponential to stationary phase. Although dicarboxylic acids were produced by each strain, no significant accumulation of pyruvate was observed for W3110, SZ47 or TC24.

Pyruvate levels in the broth of TC36 increased (16 mM at 12 h) during the transition stage (FIG. 4C). Although this pyruvate was subsequently metabolized, the excretion of pyruvate indicates that glucose uptake and glycolysis per se may not be limiting for acetate production. Because of the various mutations in TC36, metabolism of pyruvate is limited primarily to small biosynthetic needs and conversion to acetyl~CoA by the pyruvate dehydrogenase complex (FIG. 1). Although pyruvate dehydrogenase is activated by low NADH, acetyl~CoA production may be limited by the availability of free CoA. Resulting rises in pyruvate pools (FIG. 4C), would serve as an allosteric activator of phosphotransferase (Suzuki, T., 1969 "Phosphotransacetylase of *Escherichia coli* B, activation by pyruvate and inhibition by NADH and certain nucleotides" *Biochim. Biophys. Acta* 191:559-569), since phosphotransferase (pta) is the first committed step for acetate production from acetyl~CoA (FIG. 1). Gratuitous ATP hydrolysis by F1-ATPase (FIG. 1C) should ensure the availability of ADP for the final step in acetate production catalyzed by acetate kinase (ackA) (FIG. 1). Excess pyruvate can also be directly oxidized to acetate by pyruvate oxidase (poxB), an enzyme that is induced during the latter stages of growth and by environmental stress (Chang, Y.-Y., A.-Y. Wang, and J. E. Cronan, Jr., 1994 "Expression of *Escherichia coli* pyruvate oxidase (PoxB) depends on the sigma factor encoded by the rpoS (katF) gene" *Mol. Microbiol.* 11:1019-1028). Thus, pyruvate oxidase (poxB) may also contribute to acetate production by TC36.

Figure 3C:
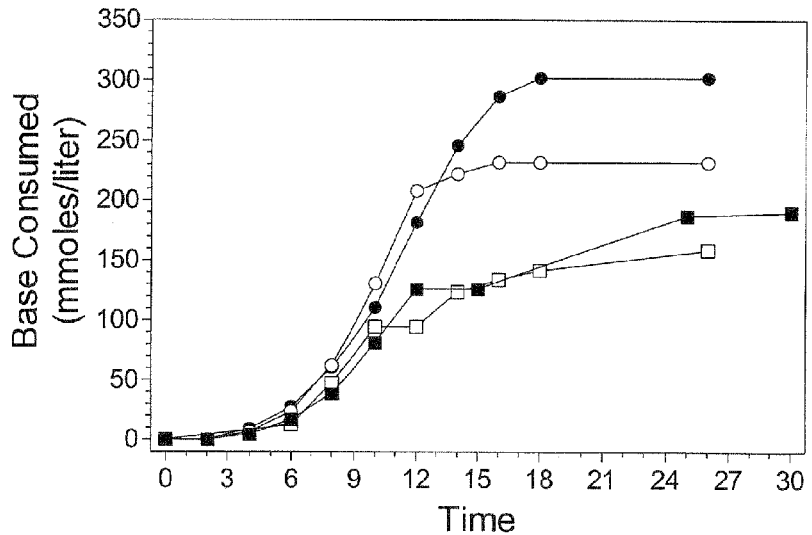

Total organic acid production can be measured by the consumption of base to maintain pH 7.0 (FIG. 3C). Consistent with a more rapid glucose metabolism, TC24 and TC36 exhibit higher rates and maxima. In general, variations in glucose utilization were accompanied by corresponding changes in base utilization. Thus, a higher consumption of base corresponds to a higher utilization of glucose. The exponential nature of the early time points reflects growth of the biocatalysts.

EXAMPLE 4

Production of Acetate

Inactivation of oxidative phosphorylation (ΔatpFH) in SZ47 to produce TC24 resulted in a 5-fold increase in acetate yield and a 3-fold improvement in carbon recovery, (Table 3), since less carbon was used in the production of cell mass. Acetate yield and carbon recovery increased by another 30% with the introduction of the sucA and adhE mutations to produce TC36. The sucA mutation disrupted the TCA cycle, while the adhE mutation blocked the production of ethanol; therefore, both mutations directed carbon atoms to the production of acetate instead of other competing products. With 3% glucose mineral salts medium, TC36 produced an average of 224 mM acetate in 16 h with only small amounts of other competing products (Table 2). This represents 68% of the maximum theoretical yield using native pathways (2 acetates per glucose), remaining carbon being divided between cell mass, dicarboxylic acids, and CO$_2$.

The maximal rates of acetate production (specific and volumetric) were approximately 2-fold higher for TC24 and TC36 than for SZ47 and W3110 (Table 3), a difference which can be attributed solely to the mutation in the (F$_1$F$_0$)H$^+$-ATP synthase. This mutation eliminated ATP production by oxidative phosphorylation while retaining cytoplasmic (F$_1$F$_0$) H$^+$-ATP synthase for the gratuitous consumption of ATP. Thus, less carbon was used in building cell mass, but rather carbon was efficiently directed to the assimilation of acetate.

The consumption of base to maintain pH 7.0 provides an overall measure of total organic acid production (FIG. 3C). Higher rates and maxima for TC24 and TC36 are consistent with more rapid glucose metabolism. In general, variations in glucose utilization were accompanied by corresponding changes in base utilization. Thus, a higher consumption of base corresponds to a higher utilization of glucose. The exponential nature of the early time points reflects growth of the biocatalysts.

EXAMPLE 5

Improving Acetate Yields

Dicarboxylic acids and cell mass were the dominant competing co-products from glucose. In order to evaluate the potential for process changes to improve acetate yield, experiments were conducted. Acetate yield was not improved by increasing the oxygen level from 5% dissolved oxygen to 15% dissolved oxygen, by reducing ammonia nitrogen (2 g $L^{-1}$ ammonium phosphate) by 40% to limit growth, or by increasing the initial concentration of glucose from 3% to 6% (Table 3).

Figure 5:
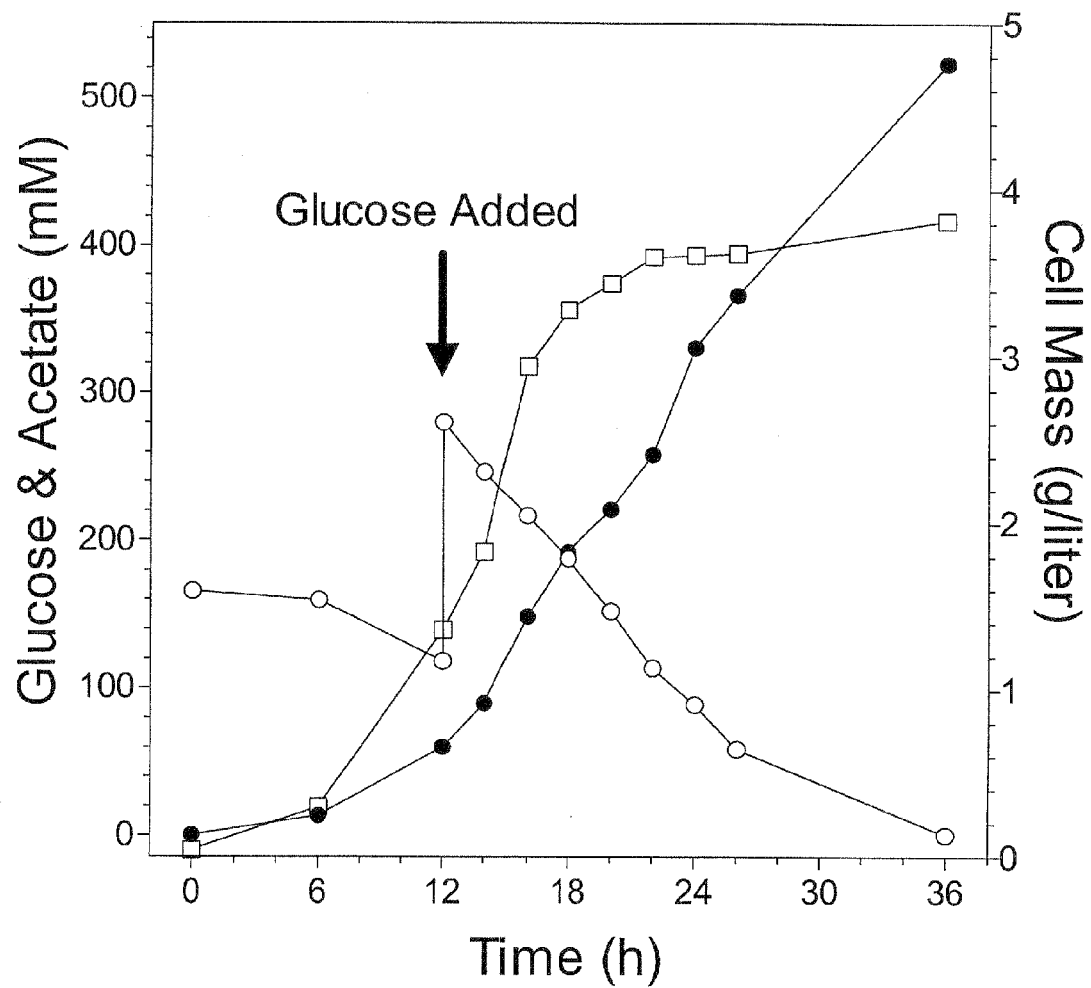
FIG. 5 Fermentation of 6% glucose to acetate by TC36 in mineral salts medium. Fermentation was begun with 3% glucose followed by a second addition of 3% glucose after 12 h. Symbols: □, cell mass; ○, glucose; ●, acetate.

However, a simple two-step batch feeding strategy was beneficial. A second addition of 3% glucose at the end of the growth phase (12 h) was metabolized to completion and produced 523 mM acetate with minimal increase in cell mass (FIG. 5). Acetate yield for this two-step addition (6% total glucose) was 78% of the theoretical maximum as compared to 68% for 3% glucose. The highest acetate yield, 86% of the theoretical maximum, was obtained by combining the one-step addition of 3% glucose with the nitrogen limitation (Table 3). Additional fed-batch experiments were conducted in which multiple additions were made to glucose levels above 100 mM. With this approach, 878 mM acetate was produced representing 75% of the maximum theoretical yield (Table 3).

Strain TC36 can be used as a biocatalysis platform for the efficient production of oxidized products. Under conditions of glucose excess, strain TC36 produced a maximum of 878 mM acetate, 75% of the maximum theoretical yield (Table 3) or 0.50 g acetate per g glucose. Along with the acetate, only cell mass and small amounts of organic acids were produced. It is likely that 878 mM acetate approaches the upper limit of tolerance for the metabolism in TC36.

Concentrations as low as 50 mM acetate have been shown to induce a stress response in *E. coli* (Kirkpatrick, C., L. M. Maurer, N. E. Oyelakin, Y. N. Yoncheva, R. Maurer, and J. L. Slonczewski, 2001 "Acetate and formate stress: Opposite responses in the proteomes of *Escherichia coli*" *J. Bacteriol.* 183:6466-6477). The minimal inhibitory concentration for growth has been previously reported as 300-400 mM acetate at neutral pH (Lasko, D. R., N. Zamboni, and U. Sauer, 2000 "Bacterial response to acetate challenge: a comparison of tolerance among species" *Appl. Microbiol. Biotechnol.* 54:243-247; Zaldivar, J., and L. O. Ingram, 1999 "Effects of organic acids on the growth and fermentation of ethanologenic *Escherichia coli* LY01" *Biotechnol. Bioengin.* 66:203-210). Oxygen transfer often becomes limiting during aerobic bioconversion processes, promoting the accumulation of reduced products (Tsai, P. S., M. Nageli, and J. E. Bailey, 2002 "Intracellular expression of *Vitreoscilla* hemoglobin modifies microaerobic *Escherichia coli* metabolism through elevated concentration and specific activity of the cytochrome o" *Biotechnol. Bioeng.* 79:558-567; Varma, A., B. W. Boesch, and B. O. Palsson, 1993 "Stoichiometric interpretation of *Escherichia coli* glucose catabolism under various oxygenation rates" *Appl. Environ. Microbiol.* 59:2465-2473).

Synthesis of reduced products was eliminated by mutations in genes (ΔfbcApflB ΔfrdCD ΔldhA ΔadhE) encoding the four major fermentation pathways. Excessive oxygen demand and NADH production were also reduced by a deletion in succinate dehydrogenase (sucAΔ). The resulting strain, TC36(ΔfocApflBΔfrdCD ΔldhA ΔatpFH ΔsucA ΔadhE) metabolizes sugars to acetate with the efficiency of fermentative metabolism, diverting a minimum of carbon to cell mass (biocatalyst) and $CO_2$. By replacing the acetate pathway, a variety of alternative oxidized products can be produced using the mutational strategies employed for the construction of TC36.

*E. coli* TC36 offers a unique set of advantages over currently employed biocatalysts for the commercial production of acetate: a single step process using sugars as substrates, high rates of acetate production, high acetate yields, simple nutrition (mineral salts), and a robust metabolism permitting the bioconversion of hexoses, pentoses, and many dissacharides.

EXAMPLE 6

Production of Pyruvic Acid

Materials and Methods

Microorganisms and media. Strains and plasmids used according to this Example 6 are listed in Table 4. Working cultures of *E. coli* W3110 (ATCC 27325) and derivatives were maintained on a minimal medium containing mineral salts (per liter: 3.5 g $KH_2PO_4$; 5.0 g $K_2HPO_4$; 3.5 g $(NH_4)_2HPO_4$, 0.25 g $MgSO_4 7H_2O$, 15 mg $CaCl_2 2 H_2O$, 0.5 mg thiamine, and 1 ml of trace metal stock), glucose (2% in plates; 3% in broth), and 1.5% agar. The trace metal stock was prepared in 0.1 M HCl (per liter: 1.6 g $FeCl_3$, 0.2 g $CoCl_2 6H_2O$, 0.1 g $CuCl_2$, 0.2 g $ZnCl_2 4H_2O$, 0.2 g $NaMoO_4$, and 0.05 g $H_3BO_3$). MOPS (0.1 M, pH 7.4) was added to both liquid and solid media when needed for pH control, but was not included in pH-controlled fermentations. During plasmid and strain construction, cultures were grown in Luria-Bertani (LB) broth or on LB plates (1.5% agar) (Miller, J. H. 1992). Glucose (2%) was added to LB medium for all strains containing mutations in $(F_1F_0)H^+$-ATP synthase. Antibiotics were included as appropriate (kanamycin, 50 mg $L^{-1}$; ampicillin, 50 mg $L^{-1}$; apramycin, 50 mg $L^{-1}$; and tetracycline, 12.5 or 6.25 mg $L^{-1}$).

Genetic Methods. Standard methods were used for plasmid construction, phage P1 transduction, electroporation, and polymerase chain reaction (PCR) (Miller, J. H., 1992 "A short course in bacterial genetics: A laboratory manual and handbook for *Escherichia coli* and related bacteria. Cold Spring Harbor Press, Cold Spring Harbor, N.Y.; Sambrook, J. and D. W. Russell, 2001 Molecular cloning: A laboratory manual. Cold Spring Harbor Press, Cold Spring Harbor, N.Y.). Chromosomal DNA served as a template to amplify ackA and poxB genes using primers (ORFiners) complementary to coding regions purchased from Sigma-Genosys, Inc. (The Woodlands, Tex.). PCR products were initially cloned into plasmid vector pCR2.1-TOPO. Integration of linear DNA was facilitated by using pKD46 (temperature conditional) containing an arabinose-inducible Red recombinase (Datsenko, K. A. & Wanner, B. L. 2000). Integrants were selected for tetracycline (6.25 mg $L^{-1}$) resistance and screened for appropriate antibiotic resistance markers and phenotypic traits. At each step, mutations were verified by analyses of PCR products and fermentation profiles. The FRT-flanked antibiotic resistance genes used for selection were deleted using a temperature-conditional plasmid (pFT-A) expressing FLP recombinase from a chlortetracycline-inducible promoter (Martinez-Morales, F., A. G. Borges, A. Martinez, K. T. Shanmugam, and L. O. Ingram, 1999 "Chromosomal integration of heterologous DNA in *Escherichia coli* with precise removal of markers and replicons during construction" *J. Bacteriol.* 181:7143-7148; Posfai, G., M. D. Koob, H. A. Kirkpatrick, and F. C. Blattner, 1997 "Versatile insertion plasmids for targeted genome manipulations in bacteria: Isolation, deletion, and rescue of the pathogenicity island LEE of the *Escherichia coli* O157:H7 genome" *J. Bacteriol.* 179: 4426-4428).

Disruption of pyruvate oxidase (poxB). The poxB coding region (1.7 kbp) was amplified by PCR using primers (ORFiners) obtained from Sigma-Genosys (The Woodlands, Tex.) and ligated into pCR2.1-TOPO. A single clone was selected in which the poxB gene was oriented in the same direction as the lac promoter (pLOI2075). To eliminate extraneous BsaBI sites in the vector, the EcoRI fragment from pLOI2075 containing poxB was ligated into the unique EcoRI site of pLOI2403 to produce plasmid pLOI2078. The small SmaI fragment (1.63 kbp) from pLOI2065 containing a tet gene flanked by FRT sites was ligated into the unique BsaBI site within the poxB gene in pLOI2078 to produce pLOI2080. After digestion with HindIII, pLOI2080 served as a template for the amplification of poxB::FRT-tet-FRT (3.4 kbp) using poxB primers. Amplified DNA was electroporated into E. coli W3110(pKD46) while expressing Red recombinase. Plasmid pKD46 was eliminated by incubation at 42° C. Double crossover recombinants were identified using antibiotic markers (tetracycline resistant; sensitive to ampicillin and kanamycin) and confirmed by PCR analysis using the poxB ORFiners (1.7 kbp fragment for W3110; 3.4 kbp fragment for mutants). One clone was selected and designated LY74.

Phage P1 was used to transduce the poxB::FRT-tet-FRT mutation from LY74 into TC36 to produce TC41. The tet gene was removed from TC41 using the FLP recombinase (pFT-A). After elimination of pFT-A by growth at 42° C., the poxB::FRT was confirmed by a comparison of PCR products using poxB primers (1.8 kbp for the mutant; 1.7 kbp for the wild type). The resulting strain was designated TC42 [(focA-pflB::FRT) frdBC::FRT, ldhA.atpFH::FRT.adhE::FRT.sucA::FRT poxB::FRT].

TABLE 4

Sources and characteristics of strains and plasmids used in Example 6.

| Strains/Plasmids | Relevant Characteristics | Reference |
| --- | --- | --- |
| | Strains | |
| W3110 | K12 wild type | ATCC 27325 |
| TOP10F' | lacI$^q$ (episome) | Invitrogen |
| LY01 | E. coli B, frd pfl::pdc$_{Zm}$ adhE$_{Zm}$ cat | Footnote[1] |
| LY74 | W3110, ΔpoxB::FRT-tet-FRT | Described herein |
| SZ61 | W3110, ΔackA::FRT-tet-FRT | Footnote[2] |
| TC36 | W3110, (Succ$^+$), Δ(focA-pflB)::FRT ΔfrdBC ΔldhA Δatp(FH)::FRT ΔadhE::FRT ΔsucA::FRT | Footnote[3] |
| TC37 | W3110, (Succ$^+$), Δ(focA-pflB)::FRT ΔfrdBC ΔldhA Δatp(FH)::FRT ΔadhE::FRT ΔsucA::FRT ΔackA::FRT-tet-FRT | Described herein |
| TC38 | W3110, (Succ$^+$), Δ(focA-pflB)::FRT ΔfrdBC ΔldhA Δatp(FH)::FRT ΔadhE::FRT ΔsucA::FRT ΔackA::FRT | Described herein |
| TC41 | W3110, (Succ$^+$), Δ(focA-pflB)::FRT ΔfrdBC ΔldhA Δatp(FH)::FRT ΔadhE::FRT ΔsucA::FRT ΔpoxB::FRT-tet-FRT | Described herein |
| TC42 | W3110, (Succ$^+$), Δ(focA-pflB)::FRT ΔfrdBC ΔldhA Δatp(FH)::FRT ΔadhE::FRT ΔsucA::FRT ΔpoxB::FRT | Described herein |
| TC43 | W3110, (Succ$^+$), Δ(focA-pflB)::FRT ΔfrdBC ΔldhA Δatp(FH)::FRT ΔadhE::FRT ΔsucA::FRT ΔpoxB::FRT ΔackA::FRT-tet-FRT | Described herein |
| TC44 | W3110, (Succ$^+$), Δ(focA-pflB)::FRT ΔfrdBC ΔldhA Δatp(FH)::FRT ΔadhE::FRT ΔsucA::FRT ΔpoxB::FRT ΔackA::FRT | Described herein |
| | Plasmids | |
| pCR2.1-TOPO | bla kan, TOPO ™ TA cloning vector | Invitrogen |
| pFT-A | bla flp low-copy vector containing recombinase and temperature-conditional pSC101 replicon | Footnote[4] |
| pKD46 | bla γ β exo low-copy vector containing red recombinase and temperature-conditional pSC101 replicon | Footnote[5] |
| pLOI2065 | bla, SmaI fragment with FRT flanked tet gene | Footnote[6] |
| pLOI2075 | bla kan poxB | Described herein |
| pLOI2078 | bla poxB | Described herein |
| pLOI2080 | bla poxB::FRT-tet-FRT | Described herein |
| pLOI2403 | bla | Footnote[7] |

[1]Yomano, L. P., S. W. York, and L. O. Ingram. 1998. Isolation and characterization of ethanol-tolerant mutants of Escherichia coli KO11 for fuel ethanol production. J. Ind. Microbiol. Biot. 20: 132-138.
[2]Zhou, S., T. B. Causey, A. Hasona, K. T. Shanmugam and L. O. Ingram. 2003. Production of optically pure D-lactic acid in mineral salts medium by metabolically engineered Escherichia coli W3110. Appl. Environ. Microbiol. 69: 399-407.
[3]Causey, T. B., S. Zhou, K. T. Shanmugam, L. O. Ingram. 2003. Engineering Escherichia coli W3110 for the conversion of sugar to redox-neutral and oxidized products: Homoacetate production. Proc. Natl. Acad. Sci, USA. 100: 825-832.
[4]Posfai, G., M. D. Koob, H. A. Kirkpatrick, and F. C. Blattner. 1997. Versatile insertion plasmids for targeted genome manipulations in bacteria: Isolation, deletion, and rescue of the pathogenicity island LEE of the Escherichia coli O157:H7 genome. J. Bacteriol.
[5]Datsenko, K. A. and B. L. Wanner. 2000. One-step inactivation of chromosomal genes in Escherichia coli K-12 using PCR products. Proc. Natl. Acad. Sci. USA 97: 6640-6645.
[6]Underwood, S. A., S. Zhou, T. B. Causey, L. P. Yomano, K. T. Shanmugam, and L. O. Ingram. 2002. Genetic changes to optimize carbon partitioning between ethanol and biosynthesis in ethanologenic Escherichia coli. Appl. Environ. Microbiol. 68: 6263-6272.
[7]Martinez-Morales, F., A. G. Borges, A. Martinez, K. T. Shanmugam, and L. O. Ingram. 1999. Chromosomal integration of heterologous DNA in Escherichia coli with precise removal of markers and replicons during construction. J. Bacteriol. 181: 7143-7148.

Deletion of ackA (acetate kinase). Phage P1 was used to transduce the ackA::FRT-tet-FRT mutation from SZ61 (Zhou, S., T. B. Causey, A. Hasona, K. T. Shanmugam and L. O. Ingram, 2003 "Production of optically pure D-lactic acid in mineral salts medium by metabolically engineered *Escherichia coli* W3110" *Appl. Environ. Microbiol.* 69:399-407) into TC36 and TC42 to produce strain TC37 [(focA-pflB::FRT) frdBC::FRT ldhA .atpFH::FRT .adhE::FRT .sucA::FRT .ackA::FRT-tet-FRT] and TC43 [(focA-pflB:: FRT) frdBC::FRT ldhA .atpFH::FRT .adhE::FRT .sucA:: FRT poxB::FRT .ackA::FRT-tet-FRT], respectively. Chromosomal integration was verified by comparison of PCR products obtained from SZ61(2.8 kbp) and W3110 (1.2 kbp) using ackA primers (ORFiners, Sigma-Genosys). A reduction in acetate production was verified for each strain by HPLC analysis of broth obtained from overnight cultures grown in mineral salts medium containing 167 mM glucose (37° C., 120-rpm). Plasmid pFT-A containing the FLP recombinase was used to excise the tet genes. After removal of this plasmid by incubation at 42° C., resulting strains were designated TC38 [(focA-pflB::FRT) frdBC::FRT ldhA .atpFH:: FRT .adhE::FRT .sucA::FRT .ackA::FRT) and TC44 [(focA-pflB::FRT)frdBC::FRT. ldhA.atpFH::FRTadhE::FRT.sucA:: FRT poxB::FRTackA::FRT], respectively.

Fermentation. Ten-liter batch fermentations (37° C., dual Rushton impellers, 450 rpm) with strain TC36 were conducted in minimal medium containing glucose (170 mM and 340 mM) using New Brunswick Bioflow 3000 fermentors (New Brunswick Scientific) as described previously (Causey, T. B., S. Zhou, K. T. Shanmugam, L. O. Ingram, 2003 "Engineering *Escherichia coli* W3110 for the conversion of sugar to redox-neutral and oxidized products: Homoacetate production" *Proc. Natl. Acad. Sci, USA* 100:825-832). Five-liter batch fermentations (37° C., dual Rushton impellers, 350 rpm) were carried out in 8 L vessels. Unless stated otherwise, dissolved oxygen levels were 100% of air saturation at the time of inoculation and allowed to fall to 5% of air saturation during continuous sparging with air (0.2 vvm). This 5% level was maintained during subsequent incubation by mixing $O_2$ with air while maintaining a constant flow rate of 1.0 L min$^{-1}$. Broth was maintained at pH 7.0 by the automatic addition of 11.4 M KOH. During fed-batch experiments, glucose was added from a sterile 4 M stock. Two fed batch regimes were investigated: 1) 3% initial glucose followed the addition of 3% glucose after 15 h (6% total); 2) 3% initial glucose with the addition of 590 ml of 4 M glucose at a constant rate over a 20-h period (9.8% total glucose).

Seed cultures were prepared by inoculating colonies from a fresh plate (48 h) into 3 ml of glucose-minimal medium (13×100 mm tube) containing 0.1 M MOPS. One ml of this cell suspension was diluted 100-fold into 1-L baffled flasks containing 200 ml of mineral salts medium (37° C., 280 rpm). When cells reached 1.0-1.5 $OD_{550nm}$, sufficient culture volume was harvested (5000×g, 25° C.) to provide an inoculum of 16.5 mg dry cell weight L$^{-1}$.

Broth samples were removed to measure organic acids, residual glucose, and cell mass. Volumetric and specific rates were estimated from measured values for glucose and acetate using GraphPad Prism (GraphPad Software, San Diego, Calif.). A smooth curve was generated with 10 points per min (Lowess method) to fit measured results. The first derivative (acetate or glucose versus time) of each curve served as an estimate of volumetric rate. Specific rates (mmoles L$^{-1}$ h$^{-1}$ mg$^{-1}$ dry cell weight) were calculated by dividing volumetric rates by respective values for cell mass.

Analyses. Organic acids and glucose were measured using a Hewlett Packard HPLC (HP 1090 series II) equipped with a UV monitor (210 nm) and refractive index detector. Products were separated using a Bio-Rad HPX-87H column (10 µl injection) with 4 mM $H_2SO_4$ as the mobile phase (0.4 ml min$^{-1}$, 45° C.). Cell mass was estimated by measuring $OD_{550nm}$ (1.0 $OD_{550nm}$ is equivalent to 0.33 g L$^{-1}$ dry cell weight) using a Bausch & Lomb Spectronic 70 spectrophotometer and 10×75 mm culture tubes as cuvettes.

Results and Methods

Figures 6A, 6B, 6C:
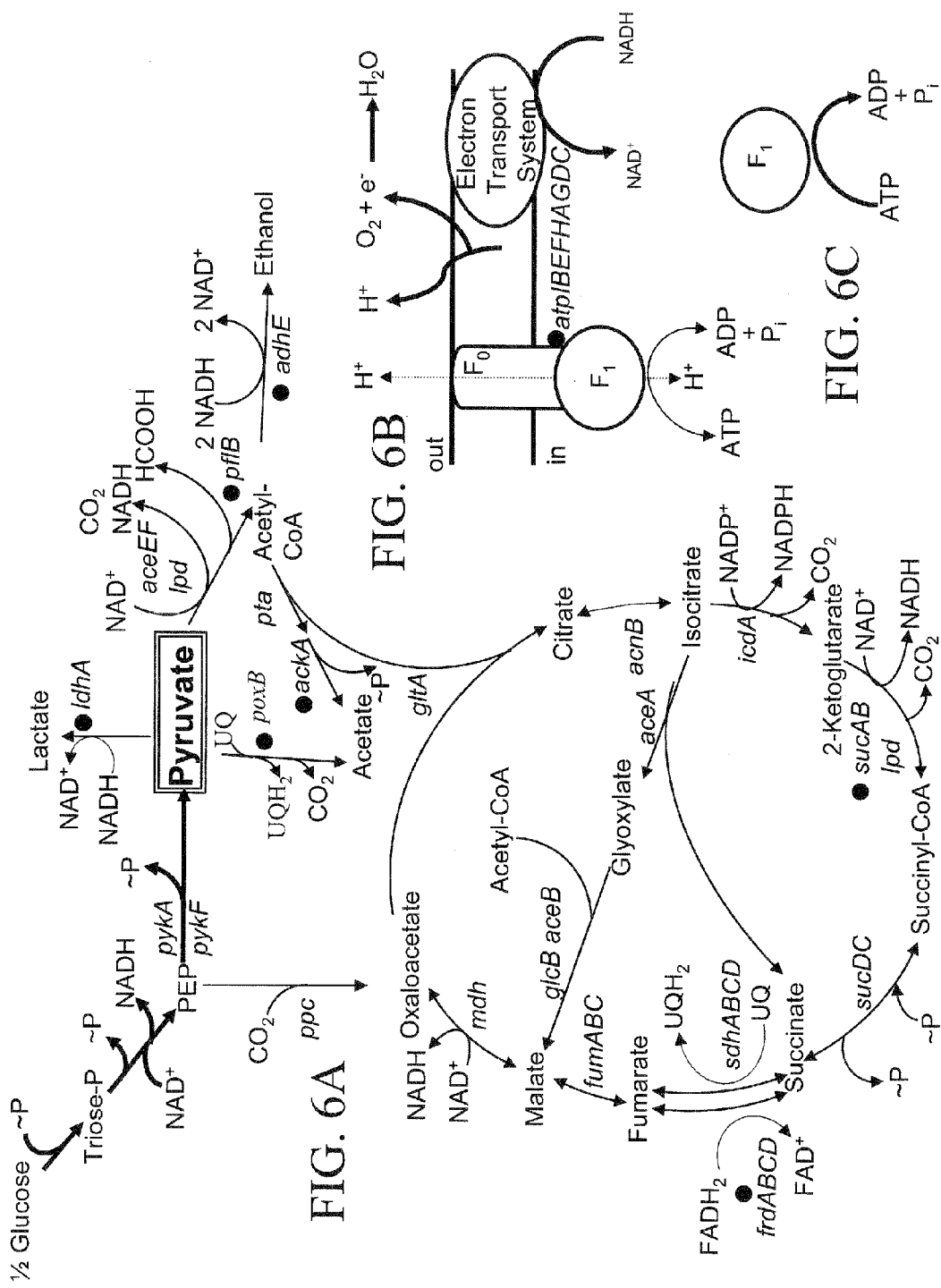
FIGS. 6A-6C Summary of central metabolism in *E. coli*. A. Carbon metabolism. B. Oxidative phosphorylation. C. Cytoplasmic $F_1$ATPase subunit (active).

Pyruvate as a co-product during acetate fermentations. *Escherichia coli* TC36 (pflB frdBC, ldhA .atpFH .adhE .sucA), as described above, was engineered from W3110 (prototrophic) for the production of acetate (FIG. 6A) by combining chromosomal deletions which minimize cell yield, fermentation products (reduced), oxygen consumption, and $CO_2$ evolution (Causey, T. B. et al. 2003). In this strain, glycolytic flux was 2-fold that of the parent W3110 due to deletion of genes (atpFH) encoding two membrane proteins that coupling the $F_1$ and $F_0$ components of the $F_1F_0(H^+)ATP$ synthase complex. This mutation eliminated ATP production by oxidative phosphorylation and also created an active, cytoplasmic $F_1(H^+)ATPase$ (FIGS. 6B and 6C). Glycolytic flux in TC36 exceeded the capacity for acetate production under the conditions used for acetate production (5% air saturation at inoculation and during fermentation) resulting in the transient accumulation of approximately 16 mM pyruvate near the end of exponential growth (FIG. 7).

Figure 7:
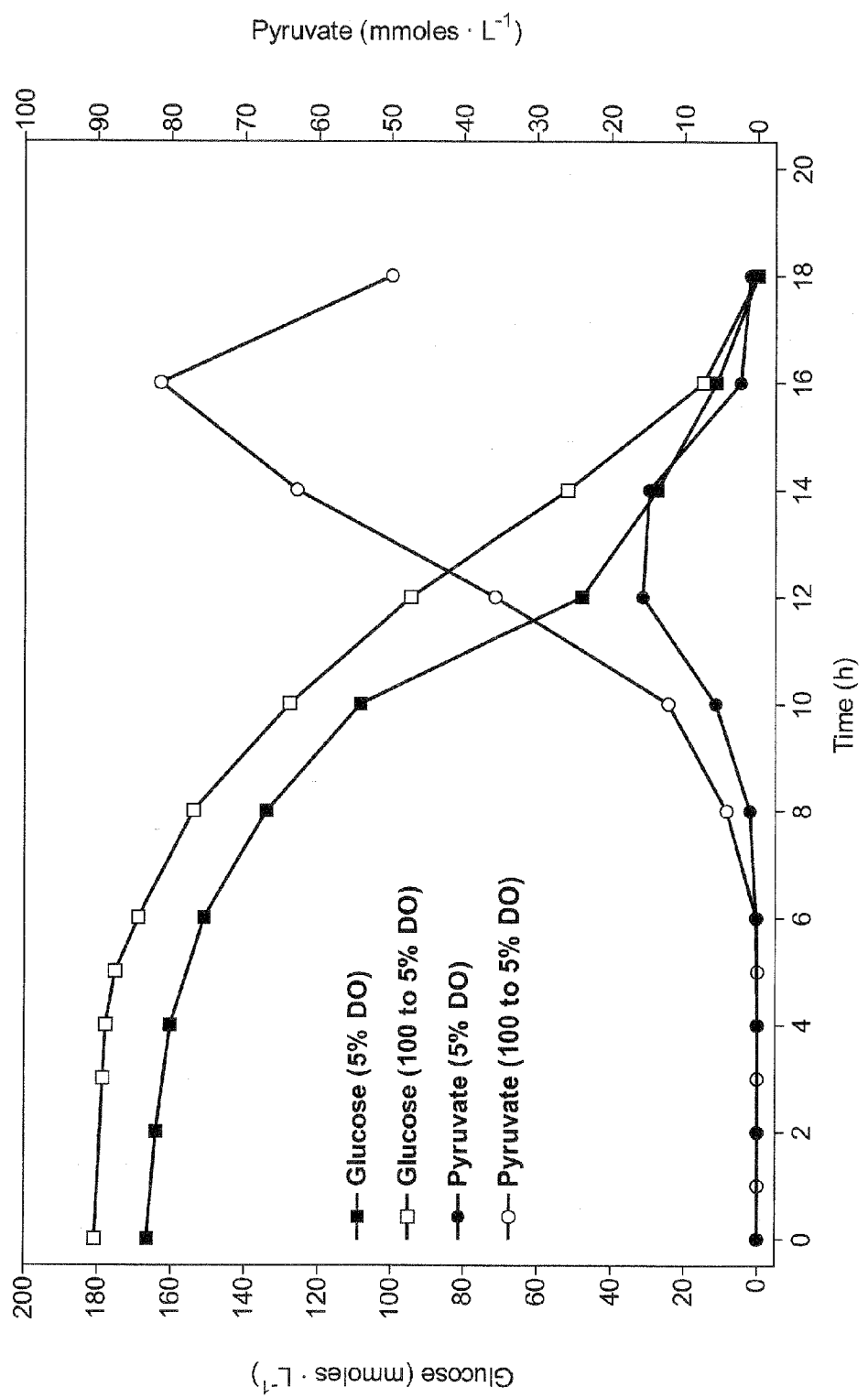
FIG. 7 Effect of oxygen level on pyruvate production by TC36. Cells were inoculated into fermentation broth at 100% air saturation and continuously sparged with air until the oxygen levels declined to 5% saturation. At this time, oxygen was blended to maintain 5% saturation during the remaining period of incubation (open symbols). Alternatively, media was sparged with a mixture of air and nitrogen to provide 5% air saturation prior to inoculation and sparging switched to air and oxygen as needed to maintain 5% air saturation (closed symbols).

By inoculating the fermentor at an initial dissolved oxygen level of 100% air saturation (rather than 5% of saturation) and sparging with air until the oxygen level declined from 100% to 5% air saturation, then adding oxygen to maintain 5% of air saturation, the peak level of pyruvate was increased to 81 mM (FIG. 7). Under these conditions, pyruvate yields were 25% of the maximum theoretical yield at the peak and 11% of the maximum theoretical yield at the end of fermentation when glucose was fully metabolized (Table 5).

Effect of an acetate kinase (ackA) mutation on pyruvate production. Although there are many metabolic routes that can lead to acetate, the primary catabolic routes for acetate production in *E. coli* are the conversion of acetyl~CoA to acetate by phosphotransacetylase (pta) and acetate kinase (ackA) and the direct oxidation of pyruvate to acetate by pyruvate oxidase (poxB) (FIG. 6A).

Figure 8A:
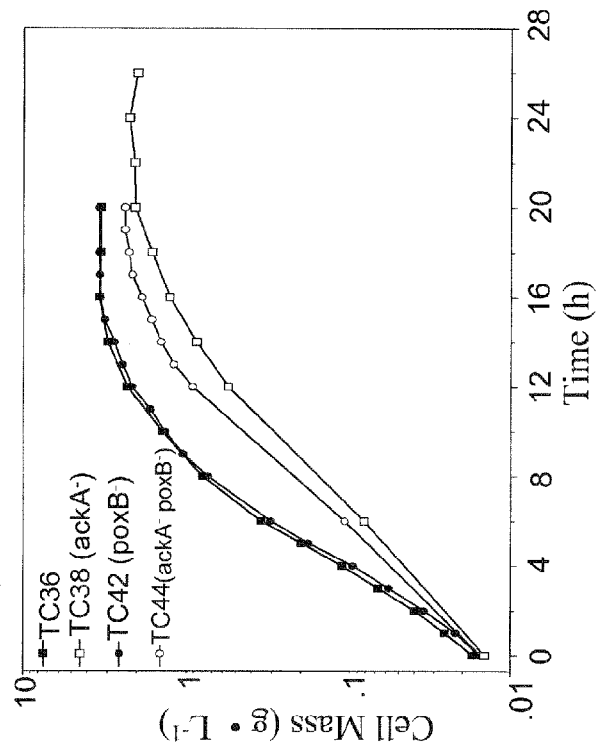
FIGS. 8A-8D Batch fermentation of glucose by mutant strains of *E. coli*. A. Cell growth; B. Glucose utilization; C. Acetate production; D. Pyruvate production.
Figure 8B:
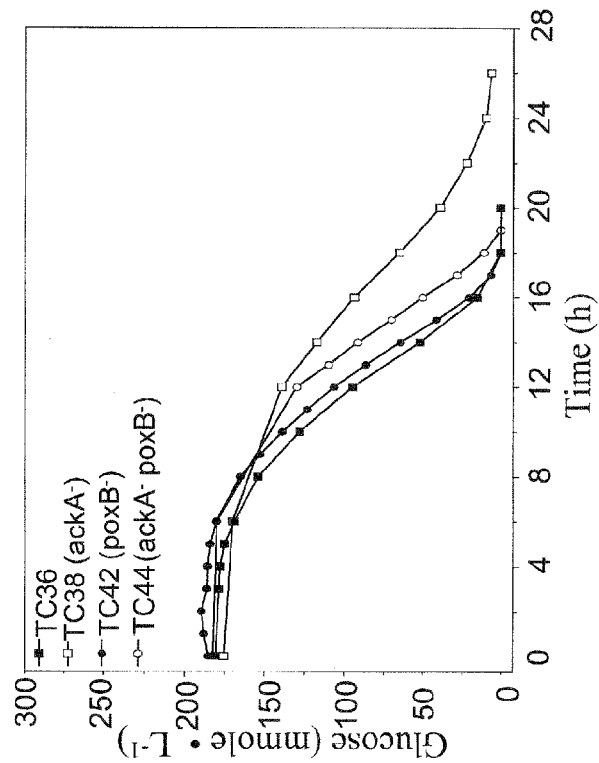

To block the acetate kinase route, strain TC38 was constructed from TC36 by deleting the central region of the ackA gene. This additional deletion reduced the net production of ATP by 30% (FIG. 6A), cell yield by 36% (FIG. 8A; Table 5), and the rate of growth by 45% (Table 6). This mutation also reduced glycolytic flux by 45% (Table 6) and increased the time required to complete fermentations from 18 h for TC36 to 24 h for TC44 (FIG. 8B). Acetate production was reduced by 85% (FIG. 8C; Table 5), consistent with the acetate kinase pathway being the dominant route for acetate production in TC36.

Figure 8D:
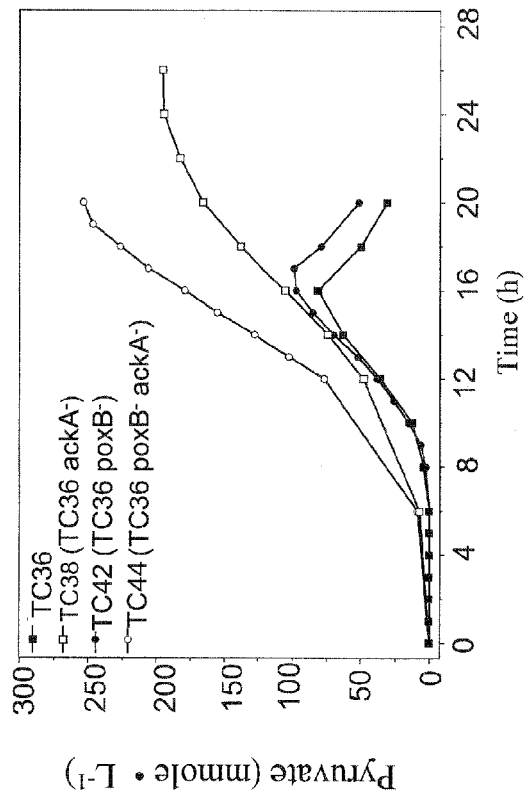

Although both volumetric and specific rates of glucose metabolism were lower for TC38 (Table 6), the pyruvate yield was 5.5-fold higher (Table 5; FIG. 8D) and the specific rate of pyruvate production was 4-fold higher (Table 6) than for TC36. Small amounts of 2-oxoglutarate, succinate, and fumarate were produced by both strains. From 10% to 15% of the carbon was not recovered as cell mass or acidic fermentation products and may have been lost as $CO_2$ due to metabolic cycling. With strain TC38, the pyruvate yield was 58% of the theoretical maximum. Acetate (28.9 mM) remained as the second most abundant product.

Effect of a pyruvate oxidase (poxB) mutation on pyruvate production. Pyruvate can be converted directly to acetate by the membrane-bound protein pyruvate oxidase using the electron transport system to couple oxygen as the terminal electron acceptor. The poxB gene is typically repressed during exponential growth but is induced by stress or entry into stationary phase (Chang, Y.-Y. and J. E. Cronan Jr. 1983; Chang, Y.-Y. et al. 1994).

Figure 8C:
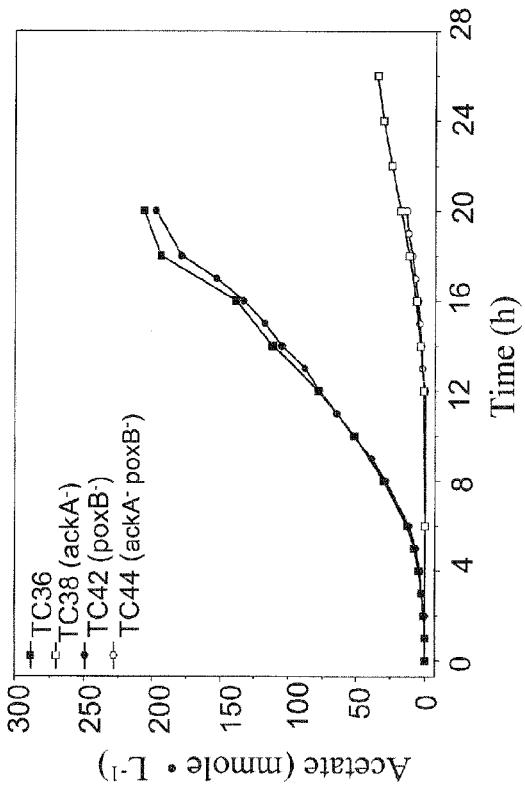

Strain. TC42 was constructed from TC36 by inserting a short DNA segment containing stop codons into the central region of poxB. In contrast to the ackA deletion (TC38), the poxB mutation (TC42) caused relatively small changes in metabolic products (Table 5) consistent with a minor role for the PoxB pathway. Acetate levels for TC42 were 10% lower and pyruvate levels were higher than for TC36 (Table 5; FIGS. 8C and 8D). Although this represented a 2-fold improvement in pyruvate yield over TC36, the overall yield for pyruvate with TC42 was less than 30% of the theoretical maximum (Table 5). These changes in metabolic products would have little effect on ATP yields (FIG. 6A). Unlike the mutation in ackA, inactivation of poxB did not reduce the rate of growth or glucose metabolism (FIG. 6A; Table 6).

Effect of combining mutations in pyruvate oxidase (poxB) and acetate kinase (ackA) on the production of pyruvate. To improve pyruvate yield and reduce acetate production, strain TC44 (pflB frdBC .ldhA .adhE sucA poxB::FRT .ackA) was constructed in which both acetate kinase and pyruvate oxidase are inactive. Inactivation of poxB was beneficial for growth and pyruvate production (FIG. 8A; Table 5 and Table 6) in comparison to TC38, an isogenic strain containing a functional poxB. Adding the poxB mutation substantially restored both volumetric and specific rates of glucose metabolism to that observed for TC36 (Table 6) in which both acetate pathways are functional, while further reducing acetate production. Acetate production by TC44 was reduced by more than half in comparison to TC38 (acetate kinase deletion) and pyruvate yield was increased by 17%. The specific rate of pyruvate production by TC44 was 8-fold that of TC36 and twice that of TC38 (Table 5). The time required to complete fermentation with TC44 was 30% shorter than with TC 38 (FIG. 8B). Broth containing 3% glucose (167 mM) was converted into 2.2% pyruvate (252 mM) after 18 h in mineral salts medium (FIG. 8D). Although acetate levels were substantially reduced by the combining of poxB and ackA mutation (FIG. 8C), acetate and dicarboxylic acids remained as minor products.

The beneficial role of a poxB mutation for pyruvate production. The pyruvate oxidase catalyzed oxidation of pyruvate to acetate (and $CO_2$) also contributes to the requirement for oxygen as an electron acceptor. Oxygen transfer rates are frequently limiting during aerobic fermentations at relatively high levels of saturation, and may be even more problematic under fermentation conditions (5% of air saturation). Eliminating the primary route for acetyl-CoA dissimilation (ackA) in TC38 increased pyruvate production and may also increase the amount of pyruvate that is metabolized by PoxB. Increasing oxygen saturation from 5% to 50% during TC38 fermentations (Table 5 and Table 6) was beneficial. Cell yield, pyruvate yield, and the specific rate of glucose metabolism were 8% to 41% higher for TC38 at 50% air saturation than at 5% air saturation. These results were very similar to those observed for the isogenic poxB mutant, TC44, during fermentation at 5% air saturation. Increasing the oxygen saturation during TC38 fermentations also decreased the final concentrations of acetate to a level equivalent to TC44 at 5% air saturation and decreased the production of dicarboxylic acids. As with TC44, low levels of acetate and dicarboxylic acids were also present at the end of fermentation with TC38 (50% air saturation) (Table 5).

Improving pyruvate yields and titers in TC44 by altering fermentation conditions. With TC44 decreasing the ammonia level by half did not increase product yields (Table 5). Doubling of the initial concentration of glucose or providing a second addition of glucose (3% plus 3%) resulted in a small increase (11%) in yield accompanied by a 2-fold increase in final pyruvate titer. The highest level of pyruvate, 749 mM, was produced with excess glucose. This may represent the limit for pyruvate tolerance. When pyruvate is added to minimal media at 600 mM, growth of wild type strains of *E. coli* is substantially inhibited.

In contrast to biocatalysts where vitamins and other complex nutrients are required for effective production of pyruvate by fermentation, the new biocatalyst of the subject invention, *E. coli* TC44, requires only mineral salts and glucose. The lack of a requirement for vitamin supplements, complex nutrients or complicated process controls for TC44 provides a substantial savings in production costs. In addition, the lack of complex nutrients in the fermentation broth reduces costs associated with product purification and waste disposal.

Pyruvate can be produced by a variety of microorganism including mutants of yeasts and bacteria. However, *E. coli* TC44 provides a competitive alternative to the current pyruvate-producing biocatalysts due to high yields, high product titers, simple fermentation conditions, and the ability to grow well in mineral salts medium with glucose as the sole carbon source (Table 7).

TABLE 5

Products formed from glucose catabolism by *E. coli* strains described herein.

| Strain | Condition | Replicates | Cell mass (g · L$^{-1}$) | Carbon Balance (%) | Pyruvate yield (% theoretical)[b] | Pyruvate | Acetate | 2-Oxoglutarate | Succinate | Fumarate |
|---|---|---|---|---|---|---|---|---|---|---|
| TC36 | 3% Glucose 5% DO[c] | 3 | 3.64 ± 0.31 | 97.9 ± 4.8 | 0.31 ± 0.22 | 1.0 ± 0.7 | 223.8 ± 14.0 | 29.0 ± 23.7 | 4.6 ± 2.2 | <0.1 |
| TC36 | 3% Glucose 100->5% DO[d] | 3 | 3.47 ± 0.23 | 89.0 ± 2.7 | 10.5 ± 7.9 | 38.1 ± 27.2[j] | 197.7 ± 21.1 | 16.6 ± 16.2 | 13.7 ± 13.2 | 1.4 ± 0.2 |
| TC38 | 3% Glucose 100->5% DO[d] | 3 | 2.21 ± 0.09 | 84.3 ± 5.2 | 57.5 ± 2.6 | 194.5 ± 9.1 | 28.9 ± 16.7 | 10.5 ± 1.9 | 8.1 ± 9.1 | 0.8 ± 0.7 |

Product Concentrations (mM)[a]

TABLE 5-continued

Products formed from glucose catabolism by *E. coli* strains described herein.

| Strain | Condition | Replicates | Cell mass (g·L$^{-1}$) | Carbon Balance (%) | Pyruvate yield (% theoretical)[b] | Pyruvate | Acetate | 2-Oxoglutarate | Succinate | Fumarate |
|---|---|---|---|---|---|---|---|---|---|---|
| TC38 | 100->50% DO[e] 3% Glucose | 2 | 2.40 | 84.7 | 68.8 | 241.9 | 7.0 | 7.9 | nd[k] | nd[k] |
| TC42 | 100->5% DO[d] 3% Glucose | 2 | 3.40 | 86.8 | 29.1 | 79.0 | 178.4 | 76.2 | 24.3 | 1.7 |
| TC44 | 100->5% DO[d] 3% Glucose ½ Nitrogen | 3 | 2.36 ± 0.10 | 88.5 ± 0.6 | 69.3 ± 1.5 | 252.5 ± 6.2 | 11.6 ± 1.2 | 3.6 ± 1.2 | 16.8 ± 0.7 | 1.1 ± 0.2 |
| TC44 | 100->5% DO[f] 3 + 3% Glucose | 2 | 2.02 | 73.6 | 38.8 | 125.2 | 50.3 | 30.0 | 7.7 | 2.9 |
| TC44 | 100->5% DO[g] 6% Glucose | 2 | 2.63 | 86.7 | 72.3 | 479.8 | 39.8 | 31.7 | 10.9 | 0.7 |
| TC44 | 100->5% DO[h] Excess Glucose | 2 | 1.95 | 94.8 | 77.9 | 588.9 | 46.0 | 26.1 | nd[k] | 0.7 |
| TC44 | 100->5% DO[i] | 2 | 2.51 | na[l] | na[l] | 749.0 | na[l] | 45.3 | na[l] | 4.9 |

Product Concentrations (mM)[a]

[a]Unless stated otherwise the concentrations represent measurements at the time of complete glucose consumption.

[b]Maximum theoretical yield is 2 moles pyruvate per mole glucose (0.978 g pyruvate g$^{-1}$ glucose).

[c]3% glucose 10 L batch fermentation with the dissolved oxygen controlled at 5% of air saturation by adjusting the ratio of O$_2$ and N$_2$ (Causey et al. 2003).

[d]3% glucose 5 L batch fermentation with the dissolved oxygen allowed to fall from 100% to 5% of air saturation.

[e]3% glucose 5 L batch fermentation with the dissolved oxygen allowed to fall from 100% to 50% of air saturation.

[f]3% glucose 5 L batch fermentation with the dissolved oxygen allowed to fall from 100% to 50% of air saturation. The (NH$_4$)$_2$PO$_4$ concentration was reduced to 1.25 g L.

[g]3% initial glucose 5 L batch fermentation with the addition of 3% glucose after 15 h. The dissolved oxygen was allowed to fall from 100% to 50% of air saturation.

[h]6% glucose 5 L batch fermentation with the dissolved oxygen allowed to fall from 100% to 50% of air saturation.

[i]3% initial glucose 5 L batch fermentation with the automatic addition of 590 ml of 4M glucose over a period of 20 h. The dissolved oxygen was allowed to fall from 100% to 50% of air saturation.

[j]The maximum pyruvate concentration measured during glucose fermentations ranged from 14.88 mM to 111.89 mM. Pyruvate excretion in TC36 is very sensitive to dissolved oxygen, where elevated dissolved oxygen results in more pyruvate being excreted. The concentration of acetate at the time all glucose has been consumed depends on the amount of pyruvate produced. Pyruvate is rapidly converted to acetate after glucose is depleted. The high standard deviations are a result of small differences in dissolved oxygen concentrations between fermentors and co-metabolism of the excreted pyruvate and glucose.

[k]Not detected.

[l]Not available

TABLE 6

Comparison of biocatalysts for pyruvate production.

| Strain | Relevant genotype/phenotype | Carbon Source | Nitrogen Source | Fermentation Time (h) | [Pyruvate] (g·L$^{-1}$) | Volumetric Production (g·L$^{-1}$ h$^{-1}$) | Pyruvate Yield (g·g$^{-1}$) | Reference |
|---|---|---|---|---|---|---|---|---|
| *Candida lipolytica* AJ 14353 | B$_1^-$ Met$^-$ | glucose | NH$_4$NO$_3$ | 72 | 44 | 0.61 | 0.44 | Footnote[1] |
| *Debaryomyces hansenii* Y-256 | B$_1^-$ Bio$^-$ | glucose | Peptone | 96 | 42 | 0.44 | 0.42 | Footnote[1] |
| *Torulopsis glabrata* AC11-3 | B$_1^-$ Bio$^-$ B$_6^-$ NA$^-$ acetate leaky | glucose | Soybean hydrolysate (NH$_4$)$_2$SO$_4$ | 47 | 60 | 1.28 | 0.68 | Footnote[1] |
| *Torulopsis glabrata* WSH-IP 303 | B$_1^-$ Bio$^-$ B$_6^-$ NA$^-$ | glucose | NH$_4$Cl | 56 | 69 | 1.23 | 0.62 | Footnote[1] |
| *Escherichia coli* TBLA-1 | lipA2 bgl$^+$ atpA401 | glucose | Polypeptone | 24 | 30 | 1.25 | 0.60 | Footnote[2] |
| *Escherichia coli* CGSC7916 | aceF fadR adhE ppc | glucose acetate | Tryptone (NH$_4$)$_2$HPO$_4$ | 36 | 35 | 0.97 | 0.65 | Footnote[3] |
| *Escherichia coli* TC44 | pflB frdBC ldhA atpFH adhE sucA ackA poxB | glucose | (NH$_4$)$_2$HPO$_4$ | 43 | 52 | 1.21 | 0.87 | Described herein |

[1]Li, Y., J. Chen, and S.-Y. Lun, and X. S. Rui, 2001 "Efficient pyruvate production by a multi-vitamin auxotroph of *Torulopsis glabrata*: key role and optimization of vitamin levels" *Appl. Microbiol. Biotechnol.* 55:680-685.
[2]Yokota, A., Y. Terasawa, N. Takaoka, H. Shimizu, and F. Tomita, 1994 "Pyruvic acid production by an F$_1$-ATPase-defective mutant of *Escherichia coli* W1485lip2" *Biosci. Biotech. Biochem.* 58:2164-2167.
[3]Tomar, A., M. A. Eiteman, and E. Altman, 2003 "The effect of acetate pathway mutations on the production of pyruvate in *Escherichia coli*." *Appl. Microbiol. Biotechnol.* 62:76-82.

TABLE 7

Comparison of metabolic rates.

| Strain | $\mu_{max}$ (h$^{-1}$) | Glucose Consumption Rate | | Pyruvate Production Rate | |
|---|---|---|---|---|---|
| | | Volumetric[a] (mmol·L$^{-1}$·h$^{-1}$) | Specific[b] (mmol·L$^{-1}$·h$^{-1}$·g$^{-1}$ cdw) | Volumetric[a] (mmol·L$^{-1}$·h$^{-1}$) | Specific[b] (mmol·L$^{-1}$·h$^{-1}$·g$^{-1}$ cdw) |
| TC36[c] (pflB frdBC ldhA atpFH adhE sucA) | 0.49 ± 0.03 | 10.1 ± 2.6 | 17.6 ± 1.5 | nd[f] | nd[f] |
| TC36[d] (pflB frdBC ldhA atpFH adhE sucA) | 0.51 ± 0.01 | 10.7 ± 0.9 | 29.7 ± 3.5 | 3.8 ± 3.0 | 5.3 ± 3.1 |
| TC38[d] (pflB frdBC ldhA atpFH adhE sucA ackA) | 0.28 ± 0.01 | 6.7 ± 0.6 | 16.3 ± 2.2 | 8.3 ± 0.7 | 21.1 ± 3.7 |
| TC38[e,g] (pflB frdBC ldhA atpFH adhE sucA ackA) | 0.21 | 6 | 28 | 8 | 28 |
| TC42[d,g] (pflB frdBC ldhA atpFH adhE sucA poxB) | 0.55 | 10 | 17 | 6 | 10 |
| TC44[d] (pflB frdBC ldhA atpFH adhE sucA poxB ackA) | 0.34 ± 0.02 | 9.7 ± 0.7 | 27.2 ± 4.1 | 13.1 ± 0.3 | 40.4 ± 7.4 |

[a]Average volumetric rates of glucose utilization and pyruvate production.
[b]Maximum specific rates of glucose utilization and pyruvate production per g dry cell weight (dcw).
[c]3% glucose 10 L batch fermentation with the dissolved oxygen controlled at 5% of air saturation by adjusting the ratio of O$_2$ and N$_2$.
[d]3% glucose 5 L batch fermentation with the dissolved oxygen allowed to fall from 100% to 5% of air saturation.
[e]Fermentation conducted with the dissolved oxygen controlled at 50% of air saturation.
[f]Not determined.
[g]Average of two experiments.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for the microbial production of a desired product comprising culturing a microbe under conditions that permit the production of a desired product selected from the group consisting of acetic acid; 1,3-propanediol; 2,3-propanediol; pyruvate; dicarboxylic acids; adipic acid; amino acids; and alcohols, wherein said microbe is TC44.

* * * * *

UNITED STATES PATENT AND TRADEMARK OFFICE
CERTIFICATE OF CORRECTION

PATENT NO. : 8,383,374 B2
APPLICATION NO. : 13/154765
DATED : February 26, 2013
INVENTOR(S) : Thomas B. Causey et al.

It is certified that error appears in the above-identified patent and that said Letters Patent is hereby corrected as shown below:

In the Specifications

Column 3,
Line 13, "2" edition." should read --$2^{nd}$ edition.--.
Line 60, "*Bacteria*" should read --*Bacteriol.*--.

Column 4,
Line 32, "Hofmeyer" should read --Hofmeyr--.
Line 33, "Hofmeyer" should read --Hofmeyr--.

Column 13,
Line 16, "vector contaiing red" should read --vector containing red--.

Column 14,
Line 32, "(ORFiners)" should read --(ORFmers)--.
Line 59, "0157:1-17" should read --O157:H7--.

Column 15,
Line 8, "pLO12065" should read --pLOI2065--.
Lines 35-36,
"(TTACTCCGTATTTGCATAAAAA -CCATGCGAGTTACGGGC CTATAAGTGTAGGCTGGAGCTGCTTC)" should read
--(TTACTCCGTATTTGCATAAAAACCATGCGAGTTACGGGC CTATAAGTGTAGGCTGGAGCTGCTTC)--.
Lines 40-42,
"TAGATTGAGTGAAGGTACGAGTAATAACGTCCTGCTGCTGTTCT CATATGAATATCCTCCTTAG" should read
--TAGATTGAGTGAAGGTACGAGTAATAACGTCCTGCTGCTGTT TCTCATATGAATATCCTCCTTAG--.

Signed and Sealed this
Thirtieth Day of July, 2013

Teresa Stanek Rea
*Acting Director of the United States Patent and Trademark Office*

CERTIFICATE OF CORRECTION (continued)
U.S. Pat. No. 8,383,374 B2

Column 16,
Line 3, "ORFiners" should read --ORFmers--.
Line 9, "(ORFiners," should read --(ORFmers,--.
Line 55, "ORFiners." should read --ORFmers.--.
Line 65, "ORFiners." should read --ORFmers.--.

Column 17,
Line 4, "ORFiners" should read --ORFmers--.
Line 26, "let gene" should read --*tet* gene--.

Column 18,
Line 44, "$\min^d$," should read --$\min^{-1}$,--.

Column 19,
Line 41, "Ingram, L. 0.," should read --Ingram, L. O.,--.

Column 20,
Line 45, "phosphylation" should read --phosphorylation--.

Column 22,
Line 66, "18 mmole $g^{-1}$" should read --18 mmole $h^{-1}$ $g^{-1}$--.

Column 25,
Line 39, "*J. Bacterial.*" should read --*J. Bacteriol.*--.
Line 57, "ΔfbcApflB" should read --*ΔfocApflB*--.

Column 26,
Line 42, "(ORFiners)" should read --(ORFmers)--.
Lines 66-67, "(ORFiners)" should read --(ORFmers)--.

Column 28,
Line 1, "ORFiners" should read --ORFmers--.
Line 5, "let gene" should read --*tet* gene--.

Column 29,
Line 10, "(ORFiners," should read --(ORFmers,--.

Column 31,
Line 35, "frdBC .ldhA .adhE" should read --frdBC ldhA atpFH adhE--.

Column 33,
Line 61, "pflB frdBC ldha" should read --pflB frdBC ldha--.

Column 34,
Line 29, "to 1.25 g L." should read --to 1.25 g $L^{-1}$.--.

UNITED STATES PATENT AND TRADEMARK OFFICE
CERTIFICATE OF CORRECTION

PATENT NO. : 8,383,374 B2
APPLICATION NO. : 13/154765
DATED : February 26, 2013
INVENTOR(S) : Thomas B. Causey et al.

It is certified that error appears in the above-identified patent and that said Letters Patent is hereby corrected as shown below:

In the Specifications

Column 3,
Line 13, "2" edition." should read --$2^{nd}$ edition.--.
Line 60, "*Bacteria*" should read --*Bacteriol.*--.

Column 4,
Line 32, "Hofmeyer" should read --Hofmeyr--.
Line 33, "Hofmeyer" should read --Hofmeyr--.

Column 13,
Line 16, "vector contaiing red" should read --vector containing red--.

Column 14,
Line 32, "(ORFiners)" should read --(ORFmers)--.
Line 59, "0157:1-17" should read --O157:H7--.

This certificate supersedes the Certificate of Correction issued July 30, 2013.

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,383,374 B2

Column 15,
Line 8, "pLO12065" should read --pLOI2065--.
Lines 35-36,
" (TTACTCCGTATTTGCATAAAAA -CCATGCGAGTTACGGGC CTATAAGTGTAGGCTGGAGCTGCTTC) " should read
--(TTACTCCGTATTTGCATAAAAACCATGCGAGTTACGGGC CTATAAGTGTAGGCTGGAGCTGCTTC)--.
Lines 40-42,
" TAGATTGAGTGAAGGTACGAGTAATAACGTCCTGCTGCTGTTCT CATATGAATATCCTCCTTAG " should read
--TAGATTGAGTGAAGGTACGAGTAATAACGTCCTGCTGCTGTTCTCATATGAATATCCTCCTTAG--.

Column 16,
Line 3, "ORFiners" should read --ORFmers--.
Line 9, "(ORFiners," should read --(ORFmers,--.
Line 55, "ORFiners." should read --ORFmers.--.
Line 65, "ORFiners." should read --ORFmers.--.

Column 17,
Line 4, "ORFiners" should read --ORFmers--.
Line 26, "let gene" should read --*tet* gene--.

Column 18,
Line 44, "$min^d$," should read --$min^{-1}$,--.

Column 19,
Line 41, "Ingram, L. 0.," should read --Ingram, L. O.,--.

Column 20,
Line 45, "phosphylation" should read --phosphorylation--.

Column 22,
Line 7, "18 mmole $g^{-1}$" should read --18 mmole $h^{-1}$ $g^{-1}$--.

Column 25,
Line 39, "*J. Bacterial.*" should read --*J. Bacteriol.*--.
Line 57, "ΔfbcApflB" should read --*AfocApflB*--.

Column 26,
Line 42, "(ORFiners)" should read --(ORFmers)--.
Lines 66-67, "(ORFiners)" should read --(ORFmers)--.

CERTIFICATE OF CORRECTION (continued)
U.S. Pat. No. 8,383,374 B2

Column 28,
Line 1, "ORFiners" should read --ORFmers--.
Line 5, "let gene" should read --*tet* gene--.

Column 29,
Line 10, "(ORFiners," should read --(ORFmers,--.

Column 31,
Line 35, "frdBC .ldhA .adhE" should read --frdBC ldhA atpFH adhE--.

Column 33,
Line 61, "pflB frdBC Idha" should read --pflB frdBC ldha--.

Column 34,
Line 29, "to 1.25 g L." should read --to 1.25 g $L^{-1}$.--.

SEQUENCE LISTING

```
<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: sense primer

<400> SEQUENCE: 1
ttactccgta tttgcataaa aaccatgcga gttacgggcc tataagtgta ggctggagct      60
gcttc                                                                  65

<210> SEQ ID NO 2
<211> LENGTH: 64
<212> TYPE: DNA
<213> ORGANISM: Artificial Sequence
<220> FEATURE:
<223> OTHER INFORMATION: antisense primer

<400> SEQUENCE: 2
tagattgagt gaaggtacga gtaataacgt cctgctgctg ttctcatatg aatatcctcc      60
ttag                                                                   64
```